(12) United States Patent
Strnad et al.

(10) Patent No.: US 6,420,137 B1
(45) Date of Patent: Jul. 16, 2002

(54) NUCLEIC ACID ENCODING HUMAN NEUROTENSIN SUBTYPE 2 RECEPTOR

(75) Inventors: Joann Strnad, Yardley, PA (US); John R. Hadcock, Eastampton, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/200,090

(22) Filed: Nov. 25, 1998

(51) Int. Cl.[7] .................. C12N 15/12; C12N 15/63; G01N 33/566; C07K 14/00
(52) U.S. Cl. ................ 435/69.1; 435/7.2; 435/320.1; 435/325; 435/455; 530/350; 536/23.5
(58) Field of Search ........................... 435/69.1, 320.1, 435/325, 455, 7.2; 530/350; 536/23.5

(56) References Cited

U.S. PATENT DOCUMENTS

| 5,668,006 A | 9/1997 | Hadcock et al. | 435/252.3 |
|---|---|---|---|
| 5,691,188 A | 11/1997 | Pausch et al. | 435/24.2 |
| 6,008,050 A | 12/1999 | Bergsma et al. | 435/455 |
| 6,022,856 A | 2/2000 | Caput et al. | 514/12 |

FOREIGN PATENT DOCUMENTS

| EP | 0 875 568 | 4/1998 | C12N/15/12 |
|---|---|---|---|
| FR | 2 760 750 | 3/1997 | C07K/14/72 |

OTHER PUBLICATIONS

Naray–Fejes–Toth, A. et al. Expression Cloning of the Adosterone Target Cell–Specific 11 b–Hydroxysteroid Dehydrogenasefrom Rabbit Collecting Duct Cells. Endocrinology. 1995. 136:2579–2586.*
Vita, N. et al. Neurotensin is an antagonist of the human neurotensin NT2 receptor expressed in Chinese hamster ovary cells. Eur J. Pharmacol. 1998. 360:265–272.*
Miyakama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc., pp. 126–128 and 228–234.*
Botto et al., FEBS Letters, 400:211–214, 1997.
Chalon et al., FEBS Letters, 386:91–94, 1996.
Chalon et al., Society for Neuroscience, 23:158.9, 1997.
Gully et al, JPET, 280:802–12, 1997.
Johnson et al., Bioorganic & Medicinal Chem. Letters, 7:561–566, 1997.
Mazella et al., J. Neuroscience, 16:5613–20, 1996.
Tanaka et al., Neuron, 4:847–854, 1990.
Vita et al., FEBS Letters, 317:139–142, 1993.
Vita et al., European Journal of Pharmacology, 360:265–272, 1998.
Fei, et al., Trends in Pharmacological Sciences, 17:1–3, 1996.
Stadel, et al., Trends in Pharmacological Sciences, 18:430–437, 1997.
Vincent, et al., Trends in Pharmacological Sciences, 20:302–309, 1999.

* cited by examiner

*Primary Examiner*—Prema Mertz
*Assistant Examiner*—Joseph F. Murphy
(74) *Attorney, Agent, or Firm*—Darby & Darby

(57) ABSTRACT

Nucleic acids encoding the long form and shorter isoform of the neurotensin receptor subtype 2, referred to as HNT2R (long) and HNT2R (short), are described. Polypeptides having amino acid sequences of the HNT2R and HNT2RS isolated proteins are also provided. A method is also provided for isolating and cloning receptors expressed from the novel HNT2R and HNT2R cDNAs for use in development/implementation of high throughput screens to identify novel neurotensin agonists and antagonists. Methods are also provided for identifying compounds that bind to HNT2R.

25 Claims, 5 Drawing Sheets

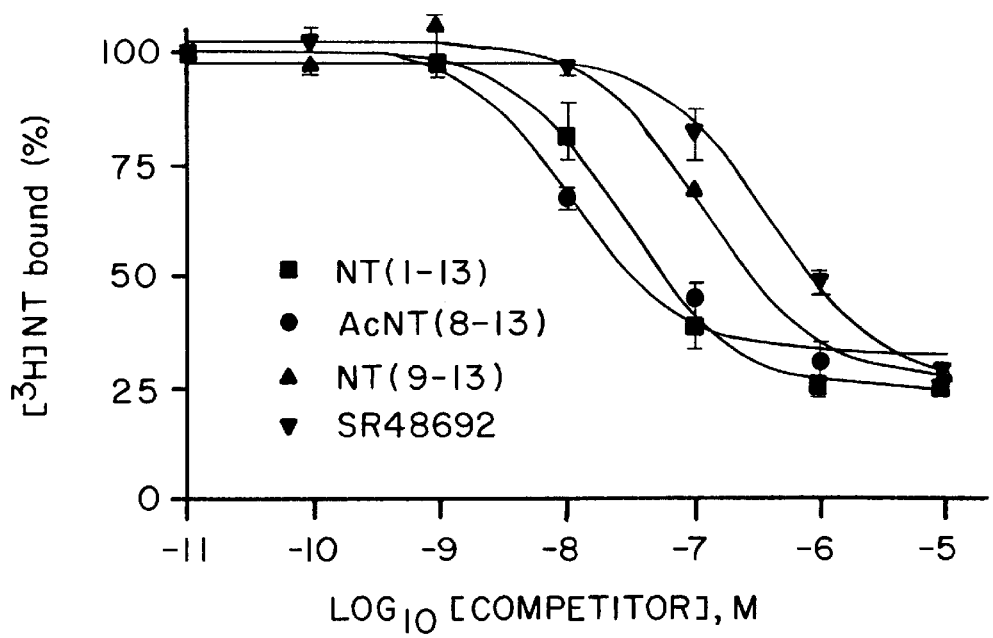
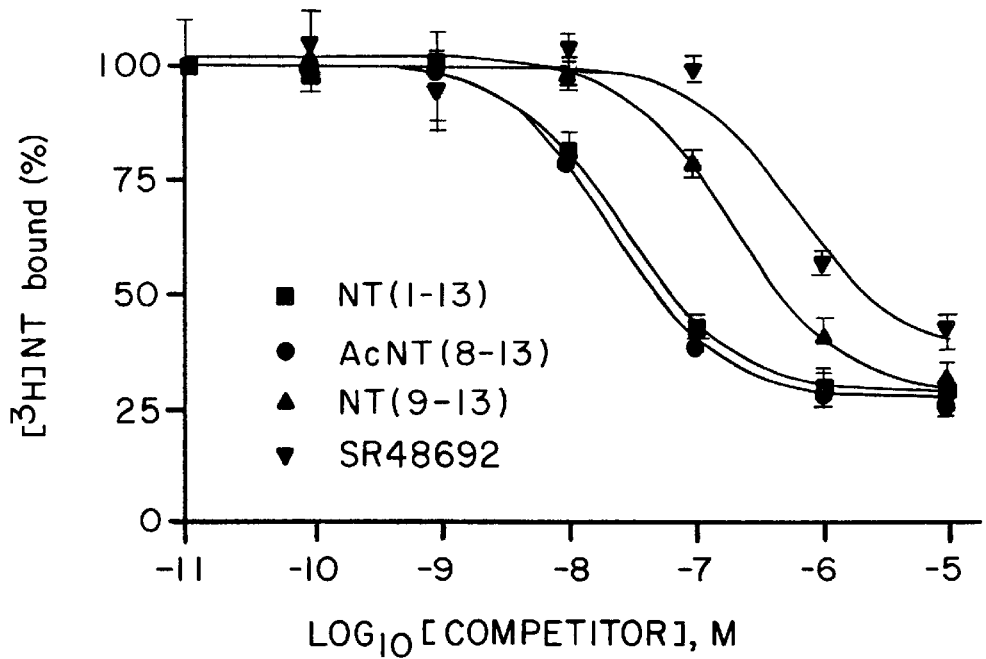

SEQUENCE LISTING

<160> NUMBER OF SEQ ID NOS: 18

<210> SEQ ID NO 1
<211> LENGTH: 1233
<212> TYPE: DNA
<213> ORGANISM: Human

<400> SEQUENCE: 1

| | | | | | |
|---|---|---|---|---|---|
| atggaaacca | gcagcccgtg | gcctccgagg | cccagcccca | gcgcagggct | gagcctggag | 60 |
| gcgcggctgg | gcgtggacac | tcgcctctgg | gccaaggtgc | tgttcaccgc | gctctactcg | 120 |
| ctcatcttag | catttggcac | agcgggctat | gcgctgtccg | tgcacgtggt | gctgaaggcg | 180 |
| cgggccggtc | gccccgggcg | cctgcgctac | cacgtgctca | gcctggcgct | ctcagccctg | 240 |
| ctgctactgc | tggtcagcgt | gcccatggag | ctctacaact | tcgtgtggtt | ccactacccc | 300 |
| tgggtcttcg | gcgacctggg | ctgccgcggc | tactacttcg | tgcacgagct | gtgcgcctac | 360 |
| gccacggtgc | tgagcgtggc | aggcctgagc | gccgagcgct | gcctagccgt | gtgccagccc | 420 |
| ctgcgtgccc | gcagcctgtt | gacgccacgc | cggacccggt | ggctggtggc | gctctcgtgg | 480 |
| gccgcctcgc | tcggcctcgc | cctgcccatg | gccgtcatca | tggggcagaa | gcacgaactc | 540 |
| gagacggcgg | acggggagcc | ggagcccgcc | tcgcgagtgt | gcacggtgct | ggtgagccgc | 600 |
| accgcgctcc | aagtctttat | ccaggtgaat | gtgctggtgt | ccttcgtgct | ccccttggca | 660 |
| ctaactgctt | tcctgaatgg | ggtcacagtg | agccacctgc | tggccctctg | ctcccaagtg | 720 |
| ccgtccactt | ctaccccggg | cagctccacc | cccagccgcc | tggagctgct | gagtgaggag | 780 |
| ggtctcctca | gcttcatcgt | atggaagaag | acctttatcc | agggaggcca | ggtcagcctg | 840 |
| gtgagacata | aagacgtgcg | ccggatccgc | agcctccagc | gcagcgtcca | ggttctcaga | 900 |
| gccatcgtgg | tcatgtatgt | catctgctgg | ctgccgtacc | atgcccgcag | gctcatgtac | 960 |
| tgctacgtac | ctgatgacgc | gtggactgac | ccactgtaca | atttctacca | ctacttctac | 1020 |
| atggtgacca | acatactttt | ctacgtcagc | tcagctgtga | ctcctcttct | ctacaacgcc | 1080 |
| gtgtcctcct | ccttcagaaa | actcttcctg | gaagccgtca | gctccctgtg | tggagagcac | 1140 |
| cacccccatga | agcggttacc | cccgaagccc | cagagtccca | ccctaatgga | tacagcttca | 1200 |
| ggctttgggg | atcccccaga | aacccggacc | tga | | | 1233 |

<210> SEQ ID NO 2
<211> LENGTH: 410
<212> TYPE: PRT
<213> ORGANISM: human

<400> SEQUENCE: 2

Met Glu Thr Ser Ser Pro Trp Pro Pro Arg Pro Ser Pro Ser Ala Gly
1               5                   10                  15

Leu Ser Leu Glu Ala Arg Leu Gly Val Asp Thr Arg Leu Trp Ala Lys
            20                  25                  30

Val Leu Phe Thr Ala Leu Tyr Ser Leu Ile Leu Ala Phe Gly Thr Ala
        35                  40                  45

Gly Tyr Ala Leu Ser Val His Val Val Leu Lys Ala Arg Ala Gly Arg
    50                  55                  60

Pro Gly Arg Leu Arg Tyr His Val Leu Ser Leu Ala Leu Ser Ala Leu
65              70                  75                  80

Leu Leu Leu Leu Val Ser Val Pro Met Glu Leu Tyr Asn Phe Val Trp
                85                  90                  95

```
Phe His Tyr Pro Trp Val Phe Gly Asp Leu Gly Cys Arg Gly Tyr Tyr
                100                 105                 110
Phe Val His Glu Leu Cys Ala Tyr Ala Thr Val Leu Ser Val Ala Gly
            115                 120                 125
Leu Ser Ala Glu Arg Cys Leu Ala Val Cys Gln Pro Leu Arg Ala Arg
        130                 135                 140
Ser Leu Leu Thr Pro Arg Arg Thr Arg Trp Leu Val Ala Leu Ser Trp
145                 150                 155                 160
Ala Ala Ser Leu Gly Leu Ala Leu Pro Met Ala Val Ile Met Gly Gln
                165                 170                 175
Lys His Glu Leu Glu Thr Ala Asp Gly Glu Pro Glu Pro Ala Ser Arg
            180                 185                 190
Val Cys Thr Val Leu Val Ser Arg Thr Ala Leu Gln Val Phe Ile Gln
        195                 200                 205
Val Asn Val Leu Val Ser Phe Val Leu Pro Leu Ala Leu Thr Ala Phe
210                 215                 220
Leu Asn Gly Val Thr Val Ser His Leu Leu Ala Leu Cys Ser Gln Val
225                 230                 235                 240
Pro Ser Thr Ser Thr Pro Gly Ser Ser Thr Pro Ser Arg Leu Glu Leu
                245                 250                 255
Leu Ser Glu Glu Gly Leu Leu Ser Phe Ile Val Trp Lys Lys Thr Phe
            260                 265                 270
Ile Gln Gly Gly Gln Val Ser Leu Val Arg His Lys Asp Val Arg Arg
        275                 280                 285
Ile Arg Ser Leu Gln Arg Ser Val Gln Val Leu Arg Ala Ile Val Val
290                 295                 300
Met Tyr Val Ile Cys Trp Leu Pro Tyr His Ala Arg Arg Leu Met Tyr
305                 310                 315                 320
Cys Tyr Val Pro Asp Asp Ala Trp Thr Asp Pro Leu Tyr Asn Phe Tyr
                325                 330                 335
His Tyr Phe Tyr Met Val Thr Asn Ile Leu Phe Tyr Val Ser Ser Ala
            340                 345                 350
Val Thr Pro Leu Leu Tyr Asn Ala Val Ser Ser Ser Phe Arg Lys Leu
        355                 360                 365
Phe Leu Glu Ala Val Ser Ser Leu Cys Gly Glu His His Pro Met Lys
370                 375                 380
Arg Leu Pro Pro Lys Pro Gln Ser Pro Thr Leu Met Asp Thr Ala Ser
385                 390                 395                 400
Gly Phe Gly Asp Pro Pro Glu Thr Arg Thr
                405                 410

<210> SEQ ID NO 3
<211> LENGTH: 1176
<212> TYPE: DNA
<213> ORGANISM: human

<400> SEQUENCE: 3
atggaaacca gcagcccgtg gcctccgagg cccagcccca gcgcagggct gagcctggac      60
gcccggctgg gcgtggacac tcgcctctgg gccaaggtgc tgttcaccgc gctctactcg     120
ctcatcttag catttggcac agcgggctat gcgctgtccg tgcacgtggt gctgaaggcg     180
cgggccggtc gccccgggcg cctgcgctac acgtgctcag gctggcgct tcagccctg      240 ctgctactgc tggtcagcgt gcccatggag ctctacaact tcgtgtggtt ccacaacccc     300
```

-continued

```
tgggtcttcg gcgacctggg ctgccgcggc tactacttcg tgcacgagct gtgcgcctac       360
gccacggtgc tgagcgtggc aggcctgagc gccgagcgct gcctagccgt gtgccagccc       420
ctgcgtgccc gcagcctgct gacgccacgc cggacccggt ggctggtggc gctctcgtgg       480
gccgcctcgc tcggcctcgc cctgcccatg gccgtcatca tggggcagaa gcacgaactc       540
gagacggcgg acggggagcc ggagcccgcc tcgcgagtgt gcacggtgct ggtgagccgc       600
accgcgctcc aagtctttat ccaggtgaat gtgctggtgt ccttcgtgct ccacttggca       660
ctaactgctt tcctaaatgg ggtcacagtg agccacatgc tggccctctg ctcccaagtg       720
ccgtccactt ctaccccggg cagctccacc cccagccgcc tggagctgct gagtgaggag       780
ggtctcctca gcttcatcgt atggaagaag acctttatcc aggggaggcc aggtcagcct       840
ggagccatcg tggtcatgta tgtcatctgc tggctgccgt accatgcccg caggctcatg       900
tactgctacg tacctgatga cgcgtggact gacccactgt acaatttcta ccactacttc       960
tacatggtga ccaacacact tttctacgtc agctcagctg tgactcctct tctctacaac      1020
gccgtgtcct cctccttcag aaaactcttc ctggaagccg tcagctccct gtgtggagag      1080
caccacccca tgaagcggtt accccgaag cccccagagtc ccaccctaat ggatacagct      1140
tcaggctttg gggatccccc agaaacccgg acctga                                1176
```

<210> SEQ ID NO 4
<211> LENGTH: 391
<212> TYPE: PRT
<213> ORGANISM: Human

<400> SEQUENCE: 4

```
Met Glu Thr Ser Ser Pro Trp Pro Pro Arg Pro Ser Pro Ser Ala Gly
  1               5                  10                  15

Leu Ser Leu Glu Ala Arg Leu Gly Val Asp Thr Arg Leu Trp Ala Lys
             20                  25                  30

Val Leu Phe Thr Ala Leu Tyr Ser Leu Ile Leu Ala Phe Gly Thr Ala
         35                  40                  45

Gly Tyr Ala Leu Ser Val His Val Leu Lys Ala Arg Ala Gly Arg
     50                  55                  60

Pro Gly Arg Leu Arg Tyr His Val Leu Ser Leu Ala Leu Ser Ala Leu
 65                  70                  75                  80

Leu Leu Leu Leu Val Ser Val Pro Met Glu Leu Tyr Asn Phe Val Trp
                 85                  90                  95

Phe His Asn Pro Trp Val Phe Gly Asp Leu Gly Cys Arg Gly Tyr Tyr
            100                 105                 110

Phe Val His Glu Leu Cys Ala Tyr Ala Thr Val Leu Ser Val Ala Gly
        115                 120                 125

Leu Ser Ala Glu Arg Cys Leu Ala Val Cys Gln Pro Leu Arg Ala Arg
    130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu His Leu Ala Leu Thr Ala Phe
    210                 215                 220
```

-continued

Leu Asn Gly Val Thr Val Ser His Met Leu Ala Leu Cys Ser Gln Val
225                 230                 235                 240

Pro Ser Thr Ser Thr Pro Gly Ser Ser Thr Pro Ser Arg Leu Glu Leu
            245                 250                 255

Leu Ser Glu Glu Gly Leu Leu Ser Phe Ile Val Trp Lys Lys Thr Phe
        260                 265                 270

Ile Gln Gly Arg Pro Gly Gln Pro Gly Ala Ile Val Met Tyr Val
        275                 280                 285

Ile Cys Trp Leu Pro Tyr His Ala Arg Arg Leu Met Tyr Cys Tyr Val
    290                 295                 300

Pro Asp Asp Ala Trp Thr Asp Pro Leu Tyr Asn Phe Tyr His Tyr Phe
305                 310                 315                 320

Tyr Met Val Thr Asn Thr Leu Phe Tyr Val Ser Ser Ala Val Thr Pro
                325                 330                 335

Leu Leu Tyr Asn Ala Val Ser Ser Ser Phe Arg Lys Leu Phe Leu Glu
            340                 345                 350

Ala Val Ser Ser Leu Cys Gly Glu His His Pro Met Lys Arg Leu Pro
        355                 360                 365

Pro Lys Pro Gln Ser Pro Thr Leu Met Asp Thr Ala Ser Gly Phe Gly
    370                 375                 380

Asp Pro Pro Glu Thr Arg Thr
385                 390

<210> SEQ ID NO 5
<211> LENGTH: 18
<212> TYPE: DNA
<213> ORGANISM: Human

<400> SEQUENCE: 5
aggccaggtc agcctgga                                                    18

<210> SEQ ID NO 6
<211> LENGTH: 6
<212> TYPE: PRT
<213> ORGANISM: Human

<400> SEQUENCE: 6

Arg Pro Gly Gln Pro Gly
1               5

<210> SEQ ID NO 7
<211> LENGTH: 25
<212> TYPE: DNA
<213> ORGANISM: Rat

<400> SEQUENCE: 7
cccatggagc tctacaactt cgtgt                                            25

<210> SEQ ID NO 8
<211> LENGTH: 27
<212> TYPE: DNA
<213> ORGANISM: Rat

<400> SEQUENCE: 8
tggggatcct caaagccgga aactgta                                          27

<210> SEQ ID NO 9
<211> LENGTH: 26
<212> TYPE: DNA

<213> ORGANISM: Human

<400> SEQUENCE: 9
gaagttgtag agctccatgg gcacgc                                  26

<210> SEQ ID NO 10
<211> LENGTH: 25
<212> TYPE: DNA
<213> ORGANISM: Human

<400> SEQUENCE: 10
cccaagtgcc gtccacttct acccc                                   25

<210> SEQ ID NO 11
<211> LENGTH: 22
<212> TYPE: DNA
<213> ORGANISM: human

<400> SEQUENCE: 11
agctatttag gtgacactat ag                                      22

<210> SEQ ID NO 12
<211> LENGTH: 22
<212> TYPE: DNA
<213> ORGANISM: Human

<400> SEQUENCE: 12
ttaatacgac tcactatagg ga                                      22

<210> SEQ ID NO 13
<211> LENGTH: 24
<212> TYPE: DNA
<213> ORGANISM: Human

<400> SEQUENCE: 13
cttcagcacc acgtgcacgg acag                                    24

<210> SEQ ID NO 14
<211> LENGTH: 22
<212> TYPE: DNA
<213> ORGANISM: Human

<400> SEQUENCE: 14
aagtgccgtc cacttctacc cc                                      22

<210> SEQ ID NO 15
<211> LENGTH: 26
<212> TYPE: DNA
<213> ORGANISM: Human

<400> SEQUENCE: 15
atgaggctga ggagaccctc ctcact                                  26

<210> SEQ ID NO 16
<211> LENGTH: 26
<212> TYPE: DNA
<213> ORGANISM: Human

<400> SEQUENCE: 16
tctacgtcag ctcagctgtg actcct                                  26

<210> SEQ ID NO 17
<211> LENGTH: 31

```
<212> TYPE: DNA
<213> ORGANISM: Human

<400> SEQUENCE: 17
aaagcttgag atggaaacca gcagcccgcg g                               31

<210> SEQ ID NO 18
<211> LENGTH: 29
<212> TYPE: DNA
<213> ORGANISM: Human

<400> SEQUENCE: 18
gctctagaat caggtccggg tttctgggg                                  29
```

NUCLEIC ACID ENCODING HUMAN NEUROTENSIN SUBTYPE 2 RECEPTOR

FIELD OF THE INVENTION

This invention relates to a novel human neurotensin receptor, designated HNT2R, present in two isoforms, a long isoform designated HNT2RL, and a deletion variant (short) form of the long isoform designated HNT2RS, and to nucleic acids encoding the human neurotensin receptor proteins. The invention further relates to high throughput screening assays with these receptors.

BACKGROUND OF THE INVENTION

Neurotensin and Neuromedin

Neurotensin is a neuropeptide that is found predominantly in the hypothalamus and gut. Neurotensin acts as a neurotransmitter and neuromodulator in the brain and as a hormone in the periphery. Native neurotensin [NT (1–13)] is a 13 amino acid peptide. However, the carboxyl terminal 6 amino acids of neurotensin (8–13) [NT (8–13)] and the more stable N-acetylated form [AcNT (8–13)] are sufficient to elicit fill biological activity mediated by neurotensin in most, but not all, tissues. A closely related peptide, neuromedin N, also binds to and activates neurotensin receptors, but with lower affinity than neurotensin. Neurotensin and neuromedin N are processed from the same precursor protein.

Neurotensin Physiology

An important response mediated by neurotensin is suppression of appetite, making this hormone a potential anti-obesity target. Both central and peripheral administration of neurotensin suppresses appetite in fed and fasted animals without altering water consumption or initiating a conditioned taste aversion (Stanley et al., Peptides 4:493–500, 1983; Hawkins, Physiol. and Behavior 36:1–8, 1986; Luttinger et al., Eur. J. Pharmacol. 81:499–503, 1982; Bailey and Flatt, Comp. Biochem. & Physiology, 84:451–4,1986). The active moiety of neurotensin is only 6 amino acids, making this potential target amenable to high throughput screens for the discovery of non-peptide agonists. Very little has been reported, however, on the chronic effects of neurotensin on metabolic responses in vivo.

Obesity

Obesity is a complex, multifactorial disease defined as a body mass index (BMI) of greater than 27 kg/m$^2$ (relative weight $\geq$120% of normal). Morbid obesity is defined as a BMI of 40 kg/m$^2$ (relative weight$\geq$200% of normal) or greater. Many genetic and environmental factors can lead to the development of obesity, including decreased resting metabolic expenditure and hyperphagia. A significant number of obese subjects have characteristic metabolic changes associated with this disease. Many are hyperinsulinemic as well as hyperglycemic indicating an insulin-resistant state, a common characteristic of non-insulin dependent diabetes mellitus (NIDDM).

The ideal anti-obesity agent would have to accomplish several tasks for it to be successful therapeutically. Three of the most important effects mediated by effective anti-obesity agents would be to increase satiety, increase metabolic energy expenditure, and increase utilization of existing fat depots (lipolytic). Most individual medical treatments for obesity either increase metabolic energy expenditure ($\beta_3$-agonists) or decrease appetite (dexfenfluramine). Very few drugs actually do both. In fact, many appetite suppressants cause a decrease in metabolic energy expenditure to compensate for the decreased energy intake. Thus, there is a need for a novel anti-obesity target that increases energy expenditure as well as decreases appetite.

Role of Neurotensin in Obesity

In animal models of obesity and in human obese patients, neurotensin levels are decreased when compared to lean animals and humans. Decreased hypothalamic neurotensin concentrations (up to 50%) have been observed in five different animal models of obesity: ob/ob, db/db, and CPE mice, and fa/faZucker and Corpulent rat models (Beck et al., Neuropeptides, 13:1–7, 1989; Williams et al., Metabolism 40:1112–16. 1991, Beck et al., J. Nutrition, 120:806–811, 1990). For ob/ob mice, the decreased hypothalamic neurotensin concentration precedes the onset of non-insulin-dependent diabetes. Decreased plasma neurotensin levels have also been observed in diabetic obese, but not diabetic lean, humans suggesting that insulin does not play a direct role in the regulation of neurotensin levels or signaling (Service et al., Regulatory Peptides 14:85–92, 1986). However, neurotensin may play a role in the regulation of insulin secretion, as high-affinity neurotensin binding sites are found in the pancreas. More importantly, the increase in plasma neurotensin levels observed in response to a meal is not observed in obese humans (Bloom et al., Anal. NY Acad. Sci. 400:105–114, 1982). Exogenously administered neurotensin suppresses appetite in lean, ob/ob, and db/db mice, suggesting that even though this important satiety signal is decreased in obesity, the signal transduction pathway is still fully functional in obese animal models.

In Vivo Studies

In vivo studies measuring the effects of AcNT(8–13) on modulation of appetite were conducted with several different mouse models of obesity. AcNT(8–13) i.p. was shown to promote biphasic suppression of food consumption in fasted ob/ob males. It was demonstrated that in animals pretreated with the NT2R-selective antagonist levocabastine, the levocabastine completely reversed the suppression of food intake mediated by 50 $\mu$g/kg AcNT(8–13), suggesting that an NT2R-like subtype mediates the NT response of feeding.

To determine whether blockade of the neurotensin response is a general phenomenon among antihistamines or specific to levocabastine, a second antihistamine, pyridine, was also tested. Pyridine exhibits high affinity binding to H1-histamine receptors but not to any NTR subtypes. Pyridine (1 mg/kg) did not block the AcNT(8–13)-mediated appetite suppression. These data indicate that the AcNT (8–13)-mediated blockade of appetite suppression by levocabastine is NTR-selective and not a general response to antihistamines.

Obesity is associated with decreased metabolic energy expenditure and increased metabolic efficiency. Increasing metabolic energy expenditure (thermogenesis) is a desirable characteristic of anti-obesity targets. AcNT(8–13), when administered acutely, displays many of the characteristics required for a good anti-obesity target, such as: appetite suppression—food consumption is suppressed 40–60%; lipolytic effects—elevated NEFAs and glycerol are observed in response to AcNT(8–13); and oxygen consumption is increased—thermogenesis is controlled by the activity of a family of proteins termed uncoupling protein (UCP); UCP uncouples respiration leading to generation of heat. Thus, there is a need in the art to identify neurotensin agonists, particularly agonists that are selective for the subtype 2 neurotensin receptor.

Neurotensin Receptor Subtypes

Based on the use of selective antagonists, three neurotensin receptor subtypes have been identified. These are designated NT1R, NT2R, and NT3R. Pharmacological data support the existence of a separate neuromedin N receptor. Thus, a fourth subtype with high affinity for the closely related peptide neuromedin N has also been proposed. Two of these receptor subtypes, NT1R and NT2R (termed high and low affinity NT binding sites), have been identified in rat by molecular cloning. All four subtypes are members of the G protein-coupled receptor superfamily and display many of the structural characteristics of this receptor family. G protein-coupled receptors, characterized by seven transmembrane domains, mediate many extracellular signals and are present in organisms as divergent as yeast and man.

Rat NT1R is a 424 amino acid polypeptide (Tanaka et al., Neuron 4:847–854, 1990; Vita et al., FEBS Letters 317:139–142, 1993). The quinoline pyrazole antagonist, SR48692 ({2-[1-(7-chloro-4-quinolinyl)-5-(2,6-dimethoxyphenyl)pyrazol-3-yl]carbonylamino]tricyclo (3,3,1,1,3,7)-decan-2-carboxyic acid}), displays a 20 to 100-fold selectivity for the NT1R over the NT2R subtype. The NT1R subtype appears to couple to at least three G protein-mediated pathways, namely, release of intracellular calcium, release of cGMP-dependent protein kinase, and modulation of adenyl cyclase activity.

Rat NT2R is a 416 amino acid polypeptide (Chalon et al., FEBS Letters 386:91–94, 1996; Marzella et al., J. Neuroscience 16:5613–20, 1996), which is 43% identical and 64% homologous to the NT1R subtype. The phenyl piperidine antagonist levocabastine (Jansenn, (–)-{3S-[1(cis)-3α4β]}-1-{4-cyano-4-(4-fluoro-phenyl)-cyclohexyl)}-3-methyl-4-phenyl-4-piperidene-carboxylic acid monohydrochloride) binds with high affinity to the NT2R subtype, and with high selectivity versus the NT1R subtype. Levocabastine exhibits a 1000-fold greater selectivity for the NT2R over the NT1R and NT3R subtypes. Levocabastine is also an antihistamine.

European Patent Publication 875 568 A1(published application) reports isolation of a putative human neurotensin receptor type 2 having 319 amino acids. Alternate splice forms yielding shorter polypeptides were also reported. The amino acid sequence reportedly was 86.86% identical (Using Bestfit) with rat NT2R (citing Chalon et al., supra for the rat NT2R). The nucelotide sequence was reported to be 79.0% identical (using Bestfit) to the rat sequence.

Little is known about the signal transduction pathways mediated by the NT2R subtype. Some neurotensin analogs elicit biological responses that cannot be ascribed to either the NT1R or NT2R subtypes. By process of elimination (responses that are not blocked by levocabastine or by SR48692), a third NT subtype has been proposed, NT3R. A third antagonist, SR142948 (2-{[5-(2,6-dimethoxyphenyl)-1-(4-(N-(3-dimethylaminopropyl)-N-methyl-carbamoyl)-2-isopropylphenyl-1H-pyrazole-3-carbonyl]-amino}adamantane-2-carboxylic acid, hydrochloride) is an antagonist that shows comparable affinity for the NT1R and NT2R subtypes but may also bind to the neuromedin N receptor (Gully et al., JPET, 280:802–812, 1997). All three antagonists display good in vivo efficacy and can be used to define the neurotensin receptor subtypes mediating physiological responses ascribed to neurotensin.

Both NT1R and NT2R are found in the primary feeding control center, the hypothalamus. NT2R messenger RNA is approximately 100-fold more abundant than NT1R mRNA in the hypothalamus. Use of SR48692 and levocabastine in vivo and in vitro can discriminate between NT1R and NT2R-mediated events.

In U.S. Pat. No. 5,668,006, G-protein linked receptors are reported to control many physiological functions, such as mediating transmembrane signaling from external stimuli (vision, taste and smell), endocrine function (pituitary and adrenal), exocrine function (pancreas), heart rate, lipolysis, and carbohydrate metabolism. The molecular cloning of a number of such receptors have revealed many structural and genetic similarities, permitting classification of the G protein-linked receptor superfamily into five distinct groups.

U.S. Pat. No. 5,691,188, describes how upon binding to the receptor, the receptor presumably undergoes a conformation change leading to activation of the G protein. G proteins are described as being comprised of three subunits: a guanyl-nucleotide binding α subunit; a β subunit; and a γ subunit. G proteins cycle between two forms, depending on whether GDP or GTP is bound to the α subunit. When GDP is bound, the G protein exists as a heterotrimer, the Gαβγ complex. When GTP is bound, the α subunit dissociates, leaving a Gβγ complex. When a Gαβγ complex operatively associates with an activated G protein coupled receptor in a cell membrane, the rate of exchange of GTP for bound GDP is increased and the rate of dissociation of the bound Gα subunit from the Gαβγ complex increases. The free Gα subunit and Gβγ complex are capable of transmitting a signal to downstream elements of a variety of signal transduction pathways. This fundamental scheme of events forms the basis for a multiplicity of different cell signaling phenomena.

In response to binding of neurotensin, the neurotensin receptor activates a G protein, which in turn modifies the activity of a variety of effector proteins. As with previously cloned receptors, hydropathy analyses of human and rat NT1R and rat NT2R sequences show seven distinct hydrophobic domains, each of which are thought to traverse the cell membrane. Both subtypes are similar in overall size, but their sequences display several differences. The amino terminus of NT1R is 33 residues longer than that of NT2R, and the third intracellular loop of NT2R is 20 residues longer than that of NT1R. The third intracellular loop of G protein coupled receptors is thought to contain sites for interaction with G proteins, thereby providing a mechanism by which extracellular signals are transduced into the cell. The differences in size as well as sequence within this loop suggest that NT1R and NT2R may couple to different G proteins, may interact differently with the same G protein, or both. The transmembrane domain 2aspartate found in many G protein-coupled receptors confers sodium sensitivity as well as coupling to certain effectors. Each of the extracellular loops of both receptor subtypes contain a cysteine residue. The DRY sequence common to many receptors, however, is an ERY in NT1R and an ERC in NT2R. The intracellular carboxyl terminus of each subtype contains a palmitoylation site as well as several serine and threonine residues, which may serve as potential phosphorylation sites.

SUMMARY OF THE INVENTION

In one embodiment, the invention provides an isolated nucleic acid comprising a sequence that encodes a functional human neurotensin subtype 2 receptor (HNT2R). In specific embodiments, the invention provides a long isoform and a short isoform of the receptor. The invention further provides vectors and host cells containing such vectors, as well as methods for expressing the HNT2R.

In a further embodiment, the invention provides an isolated nucleic acid of at least about 15 nucleotide bases that hybridizes under highly stringent conditions with a nucleic acid encoding the NTR2R.

In yet a further embodiment, the invention provides an isolated human neurotensin subtype 2 receptor (HNT2R), including both the long and short isoforms thereof. Also provided is an antibody that specifically binds to the HNT2R.

In yet another embodiment, the invention provides a method for identifying a compound that binds to HNT2R comprising detecting binding of a test compound to HNT2R.

For the first time, functional cDNA clones encoding the entire HNT2R receptor have been isolated and their expression characterized. Surprisingly, two functional isoforms have been found: HNT2RL (long), which appears to be the full length receptor polypeptide, and HNT2RS (short), which is a deletion variant (splicing variant) form of HNT2RL. Relative to HNT2RL (long), HNT2RS (short) lacks 58 nucleotides in the region encoding IC3 and TM6. The existence of HNT2RS was completely unexpected; no rat or other homolog of this isoform has been reported to date.

BRIEF DESCRIPTION OF THE DRAWINGS

FIGS. 1A and B. Competition of [$^3$H]neurotensin binding by various ligands. A: Binding to membranes from $GH_4C_1$ cells stably expressing HNT2RL. B: Binding to membranes from $GH_4C_1$ cells stably expressing HNT2RS.

DETAILED DESCRIPTION OF THE INVENTION

Figure 2A:
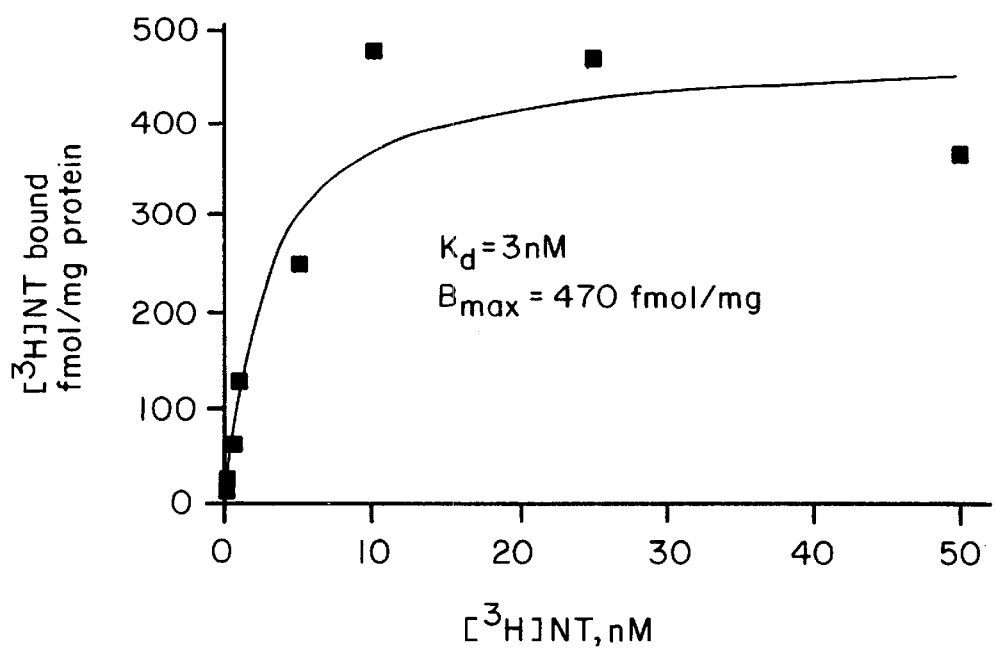
FIGS. 2A and B. [$^3$H]NT saturation binding to membranes prepared from $GH_4C_1$ cells stably expressing human NT2R. $GH_4C_1$ cells expressing this receptor were grown in media supplemented with either certified fetal bovine serum (Life Technologies) or dialyzed fetal bovine serum (Life Technologies) prior to membrane preparation. Radioligand binding was performed using 0.1–50 nM [$^3$H]NT and 40 µg membrane protein per well. $K_D$ and $B_{max}$ values were calculated using GraphPad Prism. A: Binding to membranes from cells stably expressing HNT2RL. B: Binding to membranes from cells stably expressing HNT2RS.

For the first time, functional cDNA clones encoding the entire HNT2R receptor have been isolated and their expression characterized. Surprisingly, two isoforms have been found: HNT2RL (long), which appears to be the fall length receptor polypeptide, and HNT2RS (short), which is a deletion variant form of HNT2RL. Relative to HNT2RL (long), HNT2RS (short) lacks 58 nucleotides in the region encoding intracellular domain 3 (IC3) and transmembrane domain (TM6). A unique 6-amino acid residue sequence (SEQ ID NO:6) (and corresponding 18-nucleotide nucleic acid sequence; SEQ ID NO:5) is introduced from residues 276 to 281 of SEQ ID NO:4 in HNT2R (short). The existence of HNT2RS was completely unexpected; no rat or other homolog of this isoform has been reported to date.

Furthermore, the structure of HNT2R of the present invention differs significantly and unexpectedly from HNT2R reported in EP 875,568. The HNT2R of the present invention (both long and short isoforms) is functional, as demonstrated in the Examples, infra.

More particularly, the HNT2R of the present invention contains amino acid residues from about 209 to about 300 of the sequence in SEQ ID NO:2, or amino acid residues from about 209 to about 281 of the sequence in SEQ ID NO:4. Similarly, a nucleic acid molecule comprising a sequence encoding HNT2R comprises a sequence encoding these amino acid sequences.

The term "HNT2R" as used herein refers to a human isoform of the neurotensin receptor type 2. Such a receptor is characterized by one or more of the following distinct features:

(a) it is a 410 amino acid polypeptide (long isoform) or 391 amino acid polypeptide (short isoform) with seven putative transmembrane domains, particularly transmembrane domain 5 (about amino acid residues 209 to 230 of sequence of SEQ ID NO:2 and SEQ ID NO:4) and cytoplasmic loop 3 (about amino acid residues 231 to 300 of the sequence of SEQ ID NO:2 and about amino acid residues 231 to 275 of SEQ ID NO:4).

(b) it is encoded by a cDNA of 1233 nucleotides (long isoform) or 1176 nucleotides (short isoform);

(c) the long isoform has 81% sequence identity, and 85% sequence similarity with rat NT2R at the amino acid level, and 84.5% sequence identity at the nucleotide level.

(d) it is functional. Functionality of HNT2R of the invention includes binding neurotensin or a neurotensin agonist, which can be affected by GTP; G-protein binding; and signal transduction in response to binding neurotensin or a neurotensin agonist. Signal transduction may be evaluated by intracellular calcium mobilization, cyclic AMP accumulation, activation of other G-protein coupled signal transduction pathways, reporter gene expression coupled to G-protein signal transduction, and other methods. In a preferred embodiment, neurotensin is an agonist of an HNT2R.

Thus, the present invention advantageously provides a nucleic acid encoding a human neurotensin subtype 2 receptor (HNT2R), the polypeptide encoded by this nucleic acid, cells stably expressing HNT2R, and methods for using such cells, e.g., to screen for HNT2R agonists and antagonists, particularly agonists and antagonists that are selective for a subtype 2 neurotensin receptor.

In a specific embodiment, the nucleotide sequences encoding the amino acids comprising the novel receptor protein are depicted in SEQ ID NO:1 for HNT2RL and in SEQ ID NO:3 for HNT2RS. The corresponding amino acid sequences are depicted in SEQ ID NO:2 and SEQ ID NO:4, respectively.

Receptors expressed from novel HNT2RL and HNT2R cDNAs may be expressed in eukaryotic and prokaryotic cells and can be used to develop and/or implement high throughput screens to identify novel neurotensin agonists and antagonists. These novel cDNAs may be used to help identify receptor subtype selective ligands and may be used to make chimeric and mutant neurotensin receptors which can be used to identify critical ligand binding domains as well as to determine selectivity of ligands. These novel cDNAs can be used to further investigate signal transduction systems of neurotensin receptors as well as to determine tissue distribution of receptors.

Both HNT2RL and HNT2RS cDNAs were inserted behind the CMV promoter in the pRC/CMV mammalian cell expression vector (Invitrogen) and used to stably transfect $GH_4C_1$ (rat pituitary somatomammatroph) cell line cells and SK-N-MC (human neuroepithelial cells) (both cell lines are available from the American Type Culture Collection, Manassas, Va.). Clonal cells expressing each of these receptor proteins were identified by their abilities to specifically bind [$^3$H] neurotensin. Translation of HNT2RL (long) and HNT2RS (short) cDNAs results in protein sequences which display many of the characteristics of G protein coupled receptors. The peptide sequences of these novel cDNAs may be used to generate antibodies. In particular, the segment described above, and particularly the third cytoplasmic loop, which are not found on the NT2R disclosed in EP 875 568, or the unique six amino acid segment of HNT2RS, can be used to generate antibodies.

In a specific embodiment, the present invention provides a plasmid adapted for expression in a mammalian cell, which comprises the cDNA encoding the functional neurotensin HNT2RL or HNT2RS. The term "adapted for expression in a mammalian cell" means that the regulatory elements necessary for the expression of the cDNA in the mammalian cell are present on the plasmid. The expression vectors expressing the HNT2R (both long and short isoforms) in cells are designated pRC/CMV.

In a more specific embodiment, the invention also provides a plasmid comprising the cDNA encoding a functional neurotensin HNT2R receptor, which is designated pJSHNT2R, (long isoform) and was deposited Nov. 13, 1998 with the American Type Culture Collection, Manassas, Va. (ATCC) under the terms of the Budapest Treaty, and assigned Accession No. 98986. The plasmid comprising the cDNA encoding a functional neurotensin HNT2RS which is designated pJSHNT2RS, was deposited Nov. 13, 1998 with the ATCC under the terms of the Budapest Treaty and assigned Accession No. 98987.

The invention further provides a cDNA probe useful for detecting nucleic acid encoding the HNT2R receptor comprising a nucleic acid molecule of at least about 15 nucleotides having a sequence complementary to a sequence included within the sequence shown in SEQ ID NOS:1 or 3. In a specific embodiment, such an oligonucleotide is specific for the sequence coding the unique six amino acid segment in HNT2RS (SEQ ID NO:5), which correspond to residues 276–281 (SEQ ID NO:6) of SEQ ID NO:4. It also provides antisense or triple-helix-forming oligonucleotides capable of suppressing expression of HNT2R.

Experimental results have shown that neurotensin to possess many of the properties required for a suitable anti-obesity agent. With the cloning of the second neurotensin receptor subtype, the possibility of discovering a subtype-selective agonist has become feasible. Other responses to neurotensin (or neuromedin N) can be assigned to specific receptor subtypes by use of antagonists selective for individual subtypes. Thus, the invention advantageously relates to using the receptors expressed from novel HNT2RL and HNT2RS (cDNAs and polypeptides for implementing high throughput screens for novel agonists and antagonists. Such screens can be performed in a HNT2R transfected-$CH_4C_1$ (rat pituitary somatomammotroph) cell line, SK-N-MC cell line, yeast, or bacteria.

In a specific embodiment the term "about" or "approximately" means within 20%, preferably within 10%, and more preferably within 5% of a given value or range.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The use of italics indicates a nucleic acid molecule (e.g., HNT2R, cDNA, gene, etc.); normal text indicates the polypeptide or protein.

Genes Encoding HNT2R Proteins

The present invention contemplates isolation of a gene encoding a HNT2R of the invention, including a full length, or naturally occurring form of HNT2R, and any antigenic fragments thereof from any human source.

In accordance with the present invention there may be employed conventional molecularbiology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

A "vector" is a recombinant nucleic acid construct, such as plasmid, phage genome, virus genome, cosmid, or artificial chromosome, to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an HNT2R gene is heterologous to the plasmid vector DNA in which it is inserted for cloning or expression, and it is heterologous to a non-human host cell in which it is expressed, e.g., a CHO cell.

A "nucleic acid molecule" (or alternatively "nucleic acid") refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The present invention provides antisense nucleic acids (including ribozymes), which may be used to inhibit expression of HNT2R of the invention. An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607).

Specific examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones(where phosphodiester is O—$PO_2$—O—$CH_2$). U.S. Pat. No. 5,677,437 describes heteroaromatic oligonucleotide linkages. Nitrogen linkers or groups containing nitrogen can also be used to prepare oligonucleotide mimics (U.S. Pat. Nos 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$;$NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

A "gene" is used herein to refer to a portion of a DNA molecule that includes a polypeptide coding sequence operatively associated with expression control sequences. In one embodiment, a gene can be a genomic or partial genomic sequence, in that it contains one or more introns. In another embodiment, the term gene refers to a cDNA molecule (i. e., the coding sequence lacking introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Expression control sequences", e.g., transcriptional and translational control sequences, are regulatory sequences that flank a coding sequence, such as promoters, enhancers, suppressors, terminators, and the like, and that provide for the expression of a coding sequence in a host cell. In eukaryotic cells, polyadenylation signals are control sequences. On mRNA, a ribosome binding site is an expression control sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S 1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if it contains introns) and translated into the protein encoded by the coding sequence.

A "signal sequence" is included at the beginning of the coding sequence of a protein to be expressed on the surface or in the membrane of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences are found on the HNT2R polypeptides of the invention, e.g., as exemplified infra.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of HNT2R, or to detect the presence of nucleic acids encoding HNT2R. In a further embodiment, an oligonucleotide of the invention can form a triple helix with a HNT2R DNA molecule. In still another embodiment, a library of oligonucleotides arranged on a solid support, such as a silicon wafer or chip, can be used to detect various polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al, Cell 50:667, 1987). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al, supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 85%, and most preferably at least about 90 or 95%, of the nucleotides match over the defined length of the DNA sequences. An example of such a sequence is an allelic variant of the specific HNT2R genes of the invention. Sequences that are substantially homologous can be identified by comparing the sequences using standard software available in sequence data banks or from commercial sources (BLAST, DNA Strider, DNA Star, FASTA, etc.), or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than about 80% of the amino acids are identical, or greater than about 85% are similar (functionally identical). Preferably, the similar or homologous sequences are identified by alignment using, for example, the GCG (Genetics Computer Group, Program Manual for the GCG Package, Version 7, Madison, Wis.) pileup program.

A gene encoding HNT2R, whether genomic DNA or cDNA, can be isolated from any source, particularly from a human cDNA or genomic library. Methods for obtaining HNT2R gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a brain cell library, since these are the cells that evidence highest levels of expression of HNT2R), by chemical synthesis, by cDNA cloning, or by the cloning of genomic DNA, or fragments thereof, purified from the desired cell (See, for example, Sambrook et al, 1989, supra; Glover, D. M. (ed.), 1985, DNA Cloning: A Practical Approach, MRL Press, Ltd., Oxford, U. K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired HNT2R gene may be accomplished in a number of ways. For example, a portion of a HNT2R gene exemplified infra can be purified and labeled to prepare a labeled probe, and the generated DNA may be screened by nucleic acid hybridization to the labeled probe (Benton and Davis, Science 196:180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, highest stringency hybridization conditions are used to identify a homologous HNT2R gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of HNT2R protein as disclosed herein. Thus, the presence of the gene may be detected by assays based on the physical, chemical, immunological, or functional properties of its expressed product.

The present invention also relates to cloning vectors containing genes encoding analogs and derivatives of HNT2R of the invention, that have the same or homologous functional activity as HNT2R. The production and use of derivatives and analogs related to HNT2R are within the scope of the present invention. For example, a deletion variant form of functional HNT2R can be provided. In a specific embodiment, a deletion of about 58 nucleotides of HNT2R (relative to the long isoform) was found. In a specific embodiment, the derivative or analog is functionally active, i.e., capable of exhibiting one or more functional activities associated with a full-length, wild-type HNT2R of the invention. Such functions include neurotensin binding, G protein binding and activation, and localization to the cell membrane. In another embodiment, an HNT2R chimeric construct containing a different cytoplasmic domain, e.g., having an intracellular signaling sequence from another receptor protein, can be prepared. Other chimeric or fusion proteins are also contemplated. Examples include chimeric NT1R/NT2R, GFP fusions, epitope tagged NT2R proteins, etc.

HNT2R derivatives can be made by altering encoding nucleic acid sequences by substitutions, additions or deletions that provide for functionally equivalent molecules. In a specific embodiment, infra, a deletion derivative of HNT2RL is prepared and found to have ligand binding and signal transduction properties in the assays used to evaluate the proteins. Preferably, derivatives are made that have enhanced or increased functional activity relative to native HNT2R. Alternatively, such derivatives may encode soluble fragments of HNT2R, or fragments of HNT2R that contain the extracellular domain that have the same or greater affinity for neurotensin or other ligands of HNT2R.

Due to the degeneracy of nucleotide coding sequences, other DNA sequences which encode substantially the same amino acid sequence as a HNT2R gene may be used in the practice of the present invention. These include but are not limited to allelic genes and nucleotide sequences comprising all or portions of HNT2R genes which are altered by the substitution of different codons that encode the same amino acid residue within the sequence, thus producing a silent change. Likewise, the HNT2R derivatives of the invention include, but are not limited to, those containing, as a primary amino acid sequence, all or part of the amino acid sequence of a HNT2R protein including altered sequences in which functionally equivalent amino acid residues are substituted for residues within the sequence resulting in a conservative amino acid substitution. For example, one or more amino acid residues within the sequence can be substituted by another amino acid of a similar polarity and, if present, charge, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys.

The genes encoding HNT2R derivatives and analogs of the invention can be produced by various methods known in the art. The manipulations which result in their production can occur at the gene or protein level. For example, the cloned HNT2R gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of HNT2R, care should be taken to ensure that the modified gene remains within the same translational reading frame as the HNT2R gene, uninterrupted by translational stop signals, in the gene region where the desired activity is encoded.

Additionally, the HNT2R-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. In the Examples, infra, such modifications were made to introduce restriction sites and facilitate cloning the HNT2R gene into an expression vector. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488,1984; Oliphant et al., Gene 44:177, 1986; Hutchinson et al., Proc. Natl. Acad. Sci. U.S.A. 83:710, 1986), use of TAB linkers (Pharmacia), etc. PCR techniques are preferred for site directed mutagenesis (see Higuchi, 1989, "Using PCR to Engineer DNA", in PCR Technology: Principles and Applications for DNA Amplification, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, E. coli, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E coli plasmid with sequences from the yeast $2\mu$ plasmid.

Expression of HNT2R Polypeptides

The nucleotide sequence coding for HNT2R, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, the nucleic acid encoding HNT2R of the invention is operationally associated with a promoter in an expression vector of the invention. Both cDNA and genomic sequences can be cloned and expressed under control of such regulatory sequences. An expression vector also preferably includes a replication origin.

Alternatively, an HNT2R polypeptide of the invention can be prepared using well-known techniques in peptide synthesis, including solid phase synthesis (using, e.g., BOC of FMOC chemistry), or peptide condensation techniques.

As used herein, the terms "polypeptide" and "protein" may be used interchangably to refer to the gene product (or corresponding synthetic product) of an HNT2R gene. The term "protein" may also refer specifically to the polypeptide as expressed in cells. A peptide is generally a fragment of a polypeptide, e.g., of about six or more amino acid residues.

The necessary transcriptional and translational signals can be provided on a recombinant expression vector, or they may be supplied by the native gene encoding HNT2R and/or its flanking regions.

Potential host-vector systems include but are not limited to mammalian cell systems infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A preferred expression host is a eukaryotic cell (e.g., yeast, insect, or mammalian cell). More preferred is a mammalian cell, e.g., human, rat, monkey, dog, or hamster cell. In specific embodiments, infra, HNT2R is expressed in a rat pituitary somatomammotroph cell line (e.g., $CH_4C_1$), a human neuroblastoma cell line (e.g., SK-N-MC), and a chinese hamster ovary cell line (e.g., CHO-K1).

A recombinant HNT2R protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al, 1989, supra).

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of HNT2R protein may be controlled by any promoter/enhancer element known in the art, but these regulatory elements must be functional in the host selected for expression. Promoters which may be used to control HNT2R gene expression include, but are not limited to, cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al, Proc. Natl. Acad. Sci. U.S.A. 78:1441–1445, 1981), the regulatory sequences of the met allothionein gene (Brinster et al., Nature 296:39–42, 1982); prokaryotic expression vectors such as the β-lactamase promoter (Villa-Kamaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al, Cell 38:639–646, 1984; Ornitz et al, Cold Spring Harbor Symp. Quant. Biol. 50:399–409, 1986; MacDonald, Hepatology 7:425–515,1987); insulin gene control region which is active in pancreatic beta cells (Hanahan, Nature 315:115–122, 1985), immunoglobulin gene control region which is active in lymphoid cells (Grosschedl et al., Cell 38:647–658, 1984; Adames et al., Nature 318:533–538, 1985; Alexander et al., Mol. Cell. Biol. 7:1436–1444, 1987), mouse mammary tumor virus control region which is active in testicular, breast, lymphoid and mast cells (Leder et al, Cell 45:485–495, 1986), albumin gene control region which is active in liver (Pinkert et al, Genes and Devel. 1:268–276, 1987), alpha-fetoprotein gene control region which is active in liver (Krumlauf et al., Mol. Cell. Biol. 5:1639–1648, 1985; Hammer et al., Science 235:53–58, 1987), alpha 1-antitrypsin gene control region which is active in the liver (Kelsey et al, Genes and Devel. 1:161–171, 1987), beta-globin gene control region which is active in myeloid cells (Mogram et al., Nature 315:338–340, 1985; Kollias et al., Cell 46:89–94, 1986), myelin basic protein gene control region which is active in oligodendrocyte cells in the brain (Readhead et al, Cell 48:703–712, 1987), myosin light chain-2 gene control region which is active in skeletal muscle (Sani, Nature 314:283–286, 1985), and gonadotropic releasing hormone gene control region which is active in the hypothalamus (Mason et al, Science 234:1372–1378, 1986).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMa1-C2, pET, pGEX (Smith et al., Gene 67:31–40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Yeast expression systems can also be used according to the invention to express HNT2R. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990).

Antibodies to HNT2R

According to the invention, HNT2R polypeptides produced recombinantly or by chemical synthesis, and fragments or other derivatives or analogs thereof, including fusion proteins, may be used as an immunogen to generate antibodies that recognize the HNT2R polypeptide. Such antibodies include but are not limited to polyclonal, monoclonal, chimeric, single chain, Fab fragments, and an Fab expression library. Such an antibody is specific for human HNT2R.

Various procedures known in the art may be used for the production of polyclonal antibodies to HNT2R polypeptide or derivative or analog thereof. For the production of antibody, various host animals can be immunized by injection with the HNT2R polypeptide, or a derivative (e.g., fragment or fusion protein) thereof, including but not limited to rabbits, mice, rats, sheep, goats, etc. In one embodiment, the HNT2R polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HNT2R polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al, Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). Production of human antibodies by CDR grafting is described in U.S. Pat. Nos. 5,585,089, 5,693,761, and 5,693,762 to Queen et al., and also in U.S. Pat. No. 5,225,539 to Winter and International Patent Application PCT/WO91/09967 by Adau et al. In an additional embodiment of the invention, monoclonal antibodies can be produced in germ-free animals (International Patent Publication No. WO 89/12690, published Dec. 28, 1989). In fact, according to the invention, techniques developed for the production of "chimeric antibodies" (Morrison et al., J. Bacteriol 159:870, 1984); Neuberger el al., Nature 312:604–608, 1984; Takeda et al., Nature 314:452–454, 1985) by splicing the genes from a mouse antibody molecule specific for an HNT2R polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. 4,946,778) can be adapted to produce HNT2R polypeptide-specific single chain antibodies. An additional embodiment of the invention utilizes the techniques described for the construction of Fab expression libraries (Huse et al., Science 246:1275–1281, 1989) to allow rapid and easy identification of monoclonal Fab fragments with the desired specificity for an HNT2R polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitant reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an HNT2R polypeptide, one may assay generated hybridomas for a product which binds to an HNT2R polypeptide fragment containing such epitope. For selection of an antibody specific to an HNT2R polypeptide from a particular species of animal, one can select on the basis of positive binding with HNT2R polypeptide expressed by or isolated from cells of that species of animal.

The foregoing antibodies can be used in methods known in the art relating to the localization and activity of the HNT2R polypeptide, e.g., for Western blotting, imaging HNT2R polypeptide in situ, measuring levels thereof in appropriate physiological samples, etc. using any of the detection techniques mentioned above or known in the art. Such antibodies can also be used in assays for ligand binding, e.g., as described in U.S. Pat. No. 5,679,582.

In a specific embodiment, antibodies that agonize or antagonize the activity of HNT2R polypeptide can be generated. Such antibodies can be tested using the assays described infra for identifying ligands.

Screening and Chemistry

Identification and isolation of HNT2R provides for development of screening assays, particularly for high throughput screening of molecules that up- or down-regulate the activity of HNT2R, e.g., by permitting expression of HNT2R in quantities greater than can be isolated from natural sources, or in indicator cells that are specially engineered to indicate the activity of HNT2R expressed after transfection or transformation of the cells. Accordingly, the present invention contemplates methods for identifying specific ligands of HNT2R using various screening assays known in the art. Furthermore, the invention permits identification of ligands that selectively bind HNT2R to a greater degree than to other neurotensin receptors.

Any screening technique known in the art can be used to screen for HNT2R agonists or antagonists. The present invention contemplates screens for small molecule ligands or ligand analogs and mimics, as well as screens for natural ligands that bind to and agonize or antagonize the activity of HNT2R in vivo. For example, natural products libraries can be screened using assays of the invention for molecules that agonize or antagonize HNT2R activity. Generally, compounds are tested for the ability to compete with labelled neurotensin or a neurotensin analog, such as AcNT (8–13) (collectively termed herein "a neurotensin receptor binding partner") for binding to the HNT2R. Examples of neurotensin receptor binding partners include neurotensin, N-terminal acetylated neurotensin (8–13)[AcNT(8–13)], neurotensin (9–13), SR48692, and levocabastine.

It is also possible to directly label the test compound to evaluate binding.

Knowledge of the primary sequence of the protein, and the similarity of that sequence with proteins of known function, can provide an initial clue as to the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 249:386–390, 1990; Cwirla, et al, Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al, Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like can be used to screen for HNT2R ligands according to the present invention.

In another embodiment, a yeast screening assay, useful for testing agonists and antagonists of mammalian G-protein coupled receptors, e.g., as disclosed in U.S. Pat. No. 5,482, 832, can be used.

The screening can be performed with recombinant cells that express the HNT2R, or alternatively, using purified protein, e.g., produced recombinantly, as described above. For example, the ability of labeled, soluble or solubilized HNT2R that includes the ligand-binding portion of the molecule, to bind ligand can be used to screen libraries, as described in the foregoing references. In a specific embodiment, infra, cell membranes containing recombinantly produced HNT2R (both long and short forms) were used in binding assays with various ligands.

For all animal studies Ac-Neurotensin (8–13) can be used instead of native neurotensin because it is more stable and will cross the blood brain barrier at high concentrations. The binding affinity of Ac-NT(8–13) is identical to that observed for the 13 amino acid form.

Preferred Screening Methods

There are several screening methods that available for the discovery of non-peptide NT agonists. These screens include radioligand binding, signal transduction, yeast expression, reporter assays, and structure function of existing peptide agonists and non-peptide antagonists. The NT1R subtype expressed in yeast displays pharmacological properties similar to that observed for this receptor when expressed in mammalian cells. The utilization of yeast as a screening tool can accelerate the search for novel neurotensin analogs. This technology can be utilized for screening of novel compounds that are identified in high throughput screens.

An alternative (and complimentary) approach is to utilize existing non-peptide antagonists and peptide agonists for structure/function analysis. Since the core structure of neurotensin is only 6 amino acids (MW=817), the feasibility of discovering non-peptide, orally active agonists is good. The size of this peptide is close to the upper limit (8–10 amino acids) for the discovery of non-peptide agonists for peptide hormones. Several examples of non-peptide agonists developed for peptide hormones include opiate (5 amino acids), cholecystokinin (CCK, 8 amino acids), and Growth Hormone Release Peptide (GHRP, 6 amino acids). Several non-peptide neurotensin antagonists have been described in the literature (e.g., Johnson et al, Bioorganic & Medicinal Chem. Letters, 7:561–566, 1997; Gully et al, JPET 280:802–12, 1997; and, Gully et al., PNAS, 90:65–69, 1993). The use of the antagonist structures may be helpful in the design of novel, non-peptide agonists. Another approach could be the analysis of the neurotensin peptide for the purpose of designing a non-peptide neurotensin agonist.

Radioligand Binding Assays

Radioligand binding assays allow further characterization of hits from high throughput screens as well as analogs of neurotensin agonists and antagonists. Using membranes from cells stably expressing each neurotensin receptor subtype, one point binding assays are first performed to determine how well a particular concentration, such as 25 $\mu$M, of each hit or analog displaces specific [$^3$H] NT binding from the receptor. If the hit or analog displaces $\geq$50% of the [$^3$H] NT bound, a competition binding assay is performed. Competition binding assays, as shown in the Examples, infra, evaluate the ability of increasing concentrations of competitor (the hit or any test compound analog) to displace [$^3$H] NT binding at each neurotensin receptor subtype. The resulting $K_i$ value indicates the relative potency of each hit or test compound for a particular receptor subtype. These competition binding assays allow the determination of the relative potencies of each hit or test compound at a particular receptor subtype, as well as to determine the receptor subtype selectivity of each hit or test compound.

Signal Transduction Assays

G protein coupled receptors (GPCR) are coupled to a variety of heterotrimeric G proteins, which are comprised of $\alpha$, $\beta$, and $\gamma$ subunits. Upon agonist binding to a GPCR at the cell surface, conformational changes occur within the agonist:GPCR complex which lead to the dissociation of the G protein $\alpha$ subunit from the $\beta\gamma$ subunits. The $G_\alpha$ and $G_{\beta\gamma}$ subunits then stimulate a variety of intracellular effectors, which transduce the extracellular signal to the inside of the cell. Various signal transduction systems known to be coupled to GPCRs include adenylate cyclase, phospholipase C, phospholipase $A_2$, sodium/hydrogen exchange, etc. Neurotensin receptors have been reported to be coupled to both intracellular calcium mobilization, presumably through activation of phospholipase C, and to the stimulation of adenylate cyclase via $G_q$ and $G_s$, respectively. Thus, measurements of intracellular calcium concentrations and adenylate cyclase activity indicate whether a hit or test compound is functionally behaving as an agonist or antagonist at the neurotensin receptor.

In a specific embodiment, G-protein signal transduction is coupled to expression of a reporter gene, thus permitting a reporter gene screening assay.

Calcium Mobilization Assay

Whole cells expressing the neurotensin receptor are loaded with a fluorescent dye that chelates calcium ions, such as FURA-2. Upon addition of neurotensin to these cells, neurotensin binds to the neurotensin receptors and calcium is released from the intracellular stores. The dye chelates these calcium ions. Spectrophotometric determination of the ratio for dye:calcium complexes to free dye determine the changes in intracellular calcium concentrations upon addition of neurotensin. Hits from screens and other test compounds can be similarly tested in this assay to functionally characterize them as agonists or antagonists. Increases in intracellular calcium concentrations are expected for compounds with agonist activity while compounds with antagonist activity are expected to block neurotensin stimulated increases in intracellular calcium concentrations.

Cylic AMP Accumulation Assay

Upon agonist binding, $G_s$ coupled GPCRs stimulate adenylate cyclase. Adenylate cyclase catalyzes the production of cyclic AMP from adenosine-5'-triphosphate which, in turn, activates protein kinases. $G_i$ coupled GPCRs are also coupled to adenylate cyclase, however, agonist binding to these receptors results in the inhibition of adenylate cyclase and the subsequent inhibition of cAMP. To measure the inhibition of cAMP accumulation, cells expressing $G_i$ coupled receptors must first be stimulated to elevate cAMP levels. This is achieved by treating the cells with forskolin, a diterpene that directly stimulates cAMP production. Co-incubation of cells expressing $G_i$ coupled receptors with forskolin and a functional agonist will result in the inhibition of forskolin-stimulated cAMP accumulation. For a cAMP assay, whole cells stably expressing HNT2R can be incubated with a test compound, and with forskolin plus a test compound. The cells are then lysed and cAMP levels are measured using the [$^{125}$I]cAMP scintillation proximity assay (SPA). Functional agonists of $G_s$ coupled receptors are expected to increase cAMP levels above basal levels whereas functional agonists of $G_i$ coupled receptors are expected to inhibit the forskolin-stimulated cAMP accumulation.

The present invention will be better understood by reference to the following Examples, which are provided as exemplary of the invention, and not by way of limitation.

EXAMPLE 1

Cloning Human Neurotensin Subtype 2 Receptors

Receptor Cloning. First strand cDNAs were synthesized from human cerebellum mRNA (Clontech) using Superscript reverse transcriptase and the Life Technologies cDNA synthesis kit and protocols. The first strand cDNA template was then used for PCR amplification of the human neurotensin receptor cDNAs using Deep Vent (exo-) DNA polymerase and primers 24 and 58, which are synthetic oligonucleotides derived from the published rat neurotensin subtype 2 receptor cDNA sequence. Oligonucleotides were synthesized on an Applied Biosystems DNA synthesizer.

Primer 24 5' CCCATGGAGCTCTACAACTTCGTGT 3' (SEQ ID NO:7)

Primer 58 5' TGGGGATCCTCAAAGCCGGAAACTGTA 3' (SEQ ID NO:8)

Amplification with primer pair 24 and 58 produced partial cDNA fragments of approximately 900 and 850 nucleotides, encoding HNT2RL and HNT2RS, respectively. Amplification conditions for Deep Vent (exo-) DNA polymerase were as follows: forty-five cycles of denaturation at 99° C. for 30 s, annealing at 59° C. for 20 s, and extension at 72° C. for 90 s. A final reaction at 72° C. for 5 minutes allowed all amplification products to be completely extended. All PCR amplifications were carried out with a Perkin Elmer model 2400 thermocycler.

The amplified fragments were gel purified, blunt-ended, and subcloned into the pT7Blue-3 vector (Invitrogen). Plasmid DNA from selected clones was purified and the inserts were sequenced with the Applied Biosystems dye terminator sequencing kit and the Applied Biosystems model 373A sequencer. Nucleotide sequences were analyzed with the Sequencher and DNAStar software programs.

Sequences derived from the partial HNT2R and HNT2RS cDNAs were used to design and synthesize additional oligonucleotides for use in identifying the remaining 5' and 3' ends of each receptor cDNA. The 5' and 3' regions were amplified from human adult brain (Life Technologies) and human hippocampus cDNA libraries, respectively, using the GeneAmp rTth DNA polymerase, XL PCR kit (PE Applied Biosystems) and the inverse PCR strategy (Biotechniques 22:1038–1044, June 1997). Using gene specific primers 141 and 143 inverse PCR amplified the 5' and 3' sequences of the neurotensin receptors along with the library vector sequence.

Primer 141: 5' GAAGTTGTAGAGCTCCATGGGCACGC 3' (SEQ ID NO:9)

Primer 143: 5' CCCAAGTGCCGTCCACTTCTACCCC 3' (SEQ ID NO:10)

Using the hot start technique, amplification conditions for Gene Amp rTth DNA polymerase XL were as follows: thirty-five cycles of denaturation at 94° C., 30s and annealing/extension at 68° C. for 4 to 5 minutes. A final reaction at 72° C. for 10 minutes allowed all amplification products to be fully extended.

Inverse PCR products from each of the libraries served as templates for a second round of standard PCR to amplify the 5' and 3' regions of each receptor. The second round of standard PCR required vector primers 184 and 49 encoding the SP6 and T7 promotor sequences, respectively, and nested gene-specific primers (primer 117 and primer 114).

Primer 184 (SP6 promotor): 5' AGCTATTTAGGTGACACTATAG 3' (SEQ ID NO:11)

Primer 49 (T7 promotor): 5' TTAATACGACTCACTATAGGGA 3' (SEQ ID NO:12)

Primer 117: 5' CTTCAGCACCACGTGCACGGACAG 3' (SEQ ID NO:13)

Primer 114: 5' AAGTGCCGTCCACTTCTACCCC 3' (SEQ ID NO:14)

To amplify the 5' region of the neurotensin receptors, primer pair 184 (SP6 promotor) and 117, and the inverse PCR template derived from human adult brain cDNA library, were used. Using EasyStart PCR tubes (Molecular Bio-Products), amplification conditions for AmpliTaq DNA polymerase (Perkin Elmer) were: thirty-five cycles of denaturation at 94° C., 30 s, annealing at 58° C., 20 s, and extension at 72° C., 1 minute. A final reaction at 72° C. for 5 minutes allowed complete extension of all amplified products.

To amplify the 3' region of the HNT2R and HNT2RS, primer pair 49 (T7 promotor) and 114 and the inverse PCR template derived from human hippocampus cDNA library were used. Amplification conditions were identical to those above for amplification of the 5' region. These PCR fragments were subcloned into the TA cloning vector, pCR2.1 (Invitrogen), and sequenced as described above to determine which fragments contain the 5' and 3' coding regions of the human neurotensin subtype 2 receptors.

Once the sequence of the entire coding region was identified, additional PCR was performed to create full length cDNAs of HNT2RL and HNT2RS isoforms. Using the inverse PCR strategy described above, the template for amplifying the 5' portion of each of the neurotensin receptors was created using the human adult brain cDNA library and primer pair 218 and 144. The template for amplifying the 3' portion of each receptor is described above. The 5' portion of the receptors was then amplified using the adult brain template and primer pair 217 and 218 and the 3' portions were amplified using the hippocampus template and primer pair 114 and 163.

Primer 218: 5' ATGAGGCTGAGGAGACCCTCCTCACT 3' (SEQ ID NO:15)

Primer 144: 5' TCTACGTCAGCTCAGCTGTGACTCCT 3' (SEQ ID NO:16)

Primer 217: 5' AAAGCTTGAGATGGAAACCAGCAGCCCGCGG 3' (SEQ ID NO:17)

Primer 163: 5' GCTCTAGAATCAGGTCCGGGTTTCTGGGG 3' (SEQ ID NO:18)

The PCR fragments thus created contain overlapping sequences which contain a BsaI restriction site. The 5' portion and each of the 3' portions were digested with BsaI, purified, and appropriately ligated together. A final amplification with each of the ligated receptors and primer pair 217 and 163 created full length HNT2RL and HNT2RS cDNAs. (Primer 217 encodes a HindIII restriction site and primer 163 encodes an XbaI restriction site.) Simultaneous HindIII and XbaI digestion of the full length receptor cDNAs allowed for easy cloning of each receptor fragment into mammalian cell expression vectors.

Three potential N-glycosylation sites are present in the extracellular amino terminus of NTR1 and one is present in the second extracellular domain. Corresponding domains within human NTR2 do not contain N-glycosylation sites. As with many cloned G protein coupled receptors, transmembrane domain 2 of NT1R contains an aspartate residue, though transmembrane 2 of human NT2R does not.

HNT2R of the present invention is clearly distinct from HNT2R reported in EP 875 568 A1 (the '568 Application). The HNT2R of the '568 Application comprises amino acid residues 1 to 208 and 301 to 410 (with a glutamic acid joining these two segments) of the longer isoform described in the present invention. Furthermore, there are 19 amino acid residue differences in the sequences of the N terminus (208 residues) of HNT2R of the present invention compared to the '568 Application. The C terminal region (amino acid residues 301–410 of SEQ ID NO:2 and 282–391 of SEQ ID NO:4) is similar between the two, with only one amino acid residue difference observed: amino acid residue 345 (isoleucine in SEQ ID NO:2) is threonine in the '568 Application. The HNT2R of the present invention contains all seven transmembrane domains, whereas the HNT2R of the '568 Application lacks the fifth transmembrane domain. Moreover, intracellular loop 3 is missing from the '568 Application sequence. This loop is present in HNT2R of the invention, and believed to mediate G protein binding in both the long and short forms of HNT2R of the present invention. Unlike the NT2R disclsosed in the '568 Application, the HNT2R of the present invention is functional, i.e., capable of mediating neurotensin binding and preferably, signal transduction, in response to binding of a neurotensin agonist. As shown in the Examples, infra, this is true for both the long and short forms of HNT2R of the invention. In contrast, HNT2R of the '568 Application is almost certainly non-functional (see, e.g., Botto et al., FEBS Letters 400:211–214, 1997).

The short isoform of HNT2R lacks amino acid residues from part of IC3 (281 to 295 of SEQ ID NO:2) and part of TM6 (296 to 300 of SEQ ID NO:2). Surprisingly, despite missing part of IC3 domain, the short isoform is functional, as shown below.

Mammalian Cell Expression. The HindIII and XbaI digested full-length receptor cDNAs were inserted into the pRC/CMV (Invitrogen) vector and subsequently used to transfect the $GH_4C_1$ (rat pituitary somatomammotroph) cell line and CHO-K1 cells using Stratagene's calcium phosphate transfection kit. Stable, G-418 (neomycin) resistant clones (at 750 μg/ml G-418 for $GH_4C_1$ cells at 500 μg/ml G-418 for CHO-K1 cells ) were identified and examined for their abilities to specifically bind [$^3$H] neurotensin. Clones exhibiting the best specific [$^3$H] neurotensin binding were then chosen for further study. For SK-N-MC cells, Lipofectamine Plus transfection kit (Life Technologies) was used. Stable G-418 resistant clones (selected at 500 μg/ml) were identified by radioligand binding.

Membrane preparations. Crude cell membranes of cells stably expressing neurotensin receptors were prepared as previously described (Eppler et al., J. Biol. Chem 267: 1, 1992). The adherent cells were removed from the plates with PBS and 2 mM EDTA, pelleted by centrifugation at 1,500×g for 10 minutes at 4° C., and resuspended in ice cold homogenization buffer (1 mM sodium bicarbonate, 1 mM EDTA, 1 mM EGTA, pH 7.2) containing 1×protease inhibitors (5 μg/ml leupeptin, 5 μug/ml aprotinin, 100 μg/ml bacitracin, and 100 μg/ml benzamidine). After 10 minutes on ice, the cells were lysed by dounce homogenizing for 20 strokes in a glass/glass homogenizer. The cell lysate was centrifuged at 1,500×g for 10 minutes at 4° C. to remove the nuclei and cell debris and the supernatant containing the cell membranes were harvested by centrifugation at 20,000×g for 30 minutes at 4° C. The membrane pellet was resuspended in 1×homogenization buffer containing 1×protease inhibitors and once again pelleted. The membrane pellet was then resuspended at 1–5 mg/ml in 25 mM Tris, pH 7.4 and either directly used in binding assays or frozen (−80° C.) in small aliquots for future use. Leupeptin was purchased from Bachem and aprotinin, bacitracin, and benzamidine are purchased from Sigma.

Radioligand binding assays: competition binding. All radioligand binding assays were performed in 96-well microtiter plates using 1×binding buffer (50 mM HEPES, pH 7.4, 10 mM $MgCl_2$, 0.2% BSA, pH 7.4) containing protease inhibitors (5 μg/ml leupeptin, 5 μmg/ml aprotinin, 100 μg/ml bacitracin, and 100 μg/ml benzamidine). All components were diluted in 1×binding buffer containing protease inhibitors and added to the microtiter plate wells in the order shown below (Table 1): binding buffer, non-radiolabeled ligand or competitor, [$^3$H]neurotensin (New England Nuclear, 100 Ci/mmol, original stock is 9 μM). Binding reactions were initiated by adding 5–100 μg of membrane protein in a 170 μl volume. Final reaction volume was 200 μl/well.

TABLE 1

Radioligand Binding Assay Conditions

| Well | Buffer | Cold Competitor | [Final] Competitor | 200 nM [$^3$H]NT | Volume of Membrane |
|------|--------|-----------------|--------------------|--------|---------------------|
| AB1 | 20 μl | 0 μl | 0 | 10 μl | 170 μl |
| AB2 | 0 | 20 μl | −12 M | 10 μl | 170 μl |
| AB3 | 0 | 20 μl | −11 M | 10 μl | 170 μl |
| AB4 | 0 | 20 μl | −10 M | 10 μl | 170 μl |
| AB5 | 0 | 20 μl | −9 M | 10 μl | 170 μl |
| AB6 | 0 | 20 μl | −8 M | 10 μl | 170 μl |
| AB7 | 0 | 20 μl | −7 M | 10 μl | 170 μl |
| AB8 | 0 | 20 μl | −6 M | 10 μl | 170 μl |
| AB9 | 0 | 20 μl | −5 M | 10 μl | 170 μl |

The microtiter plate was placed on a rotary shaker at 200 rpm and incubated at room temperature for 2 hours. Free radioligand was separated from bound ligand by rapid filtration through a glass fiber (GF/C) filter plate pretreated with 0.3% polyethyleneimine for 30 minutes) using a Packard cell harvester. The filter plates were then washed several times with cold water (4° C.) binding buffer lacking BSA. After the filter plates were dried in a 37° C. incubator for 2 hours, 25 μl Microscint scintillation fluid (Packard) was added to each well and the plate was counted in a Packard Top Count scintillation counter.

The results of this assay are shown in FIG. 1. Both the long (FIG. 1A) and the short (FIG. 1B) forms of HNT2R bound NT(1–13) and AcNT(8–13) equally well. As expected, for both receptor isoforms, the NT1R-specific antagonist SR48692 competed at a concentration about two orders of magnitude higher than that of either NT or AcNT (8–13). NT(9–13), like SR48692 bound with lower affinity as well.

Radioligand binding assays: saturation binding. All radioligand binding assays were performed in 96-well microtiter plates. All components were diluted in 1×binding buffer containing 1×protease inhibitors and added to the microtiter plate wells in the following order: binding buffer in wells 1 and 2, non-radiolabeled neurotensin to wells 3 and 4, 10 μl of appropriate concentration of stock [$^3$H]neurotensin to wells 1 through 4. Binding reactions were initiated by adding 5–50 μg of membrane protein in a 170 μl volume into each well. Final reaction volume was 200 μl/well.

TABLE 2

Saturation Binding Assay Conditions

| Well | Buffer (wells 1,2) | 100 μM NT (wells 3,4) | [³H]NT (nM) | Buffer | Stock [³H]NT | [³H]NT Volume | Final [³H]NT (nM) | ss Volume Membrane |
|---|---|---|---|---|---|---|---|---|
| A1-4 | 20 | 20 | 2.5* | 97.5 | 2 | 10 | 0.1 | 170 |
| B1-4 | 20 | 20 | 5.0* | 95.0 | 5 | 10 | 0.25 | 170 |
| C1-4 | 20 | 20 | 10.0* | 90.0 | 10 | 10 | 0.5 | 170 |
| D1-4 | 20 | 20 | 20.0* | 80.0 | 20 | 10 | 1.0 | 170 |
| E1-4 | 20 | 20 | 2.2 | 197.8 | 100 | 10 | 5.0 | 170 |
| F1-4 | 20 | 20 | 2.2 | 97.8 | 200 | 10 | 10.0 | 170 |
| G1-4 | 20 | 20 | 5.5 | 95.5 | 500 | 10 | 25.0 | 170 |
| H1-4 | 20 | 20 | 11.0 | 89.0 | 1000 | 10 | 50.0 | 170 |

*volumes of 100 nM [³H]NT

All volumes in Table 2 are in microliters.

The microtiter plate was placed on a rotary shaker set at 200 rpm and incubated at room temperature for 2 hours. Free radioligand were separated from bound ligand by rapid filtration through a glass fiber (GF/C) filter plate (pretreated with 0.3% polyethyleneimine for 30 minutes) using a Packard cell harvester. The filter plates were then washed several times with cold (4° C.) binding buffer lacking BSA. After the filter plates were dried in a 37° C. incubator for 2 hours, 25 μl Microscint scintillation fluid (Packard) was added to each well and the plate was counted in a Packard Top Count scintillation counter.

Figure 2B:
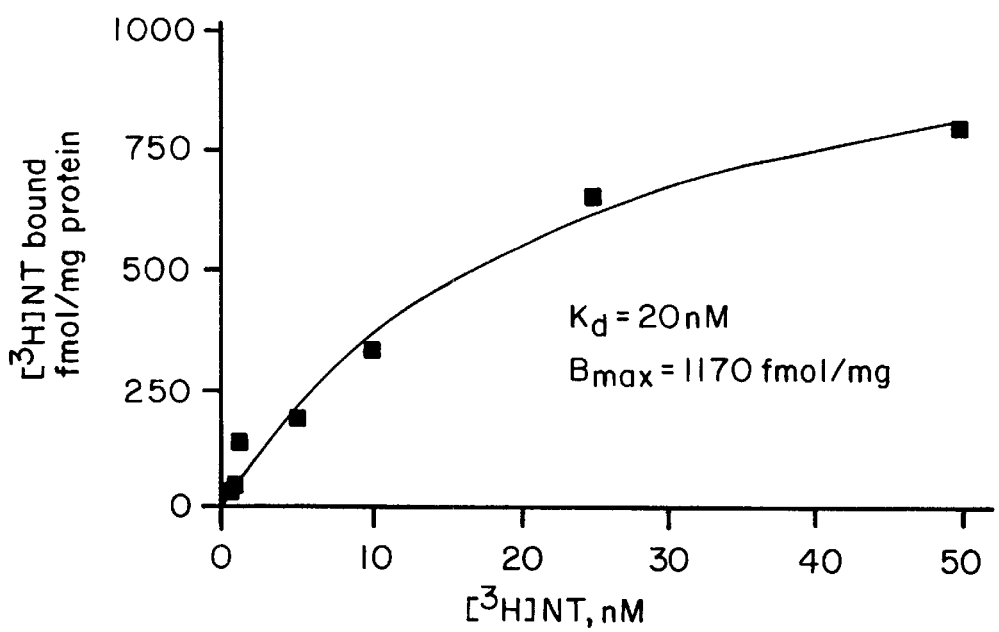

The results of this assay are shown in FIG. 2. The HNT2RL isoform bound neurotensin with greater apparent affinity than HNT2RS (compare FIGS. 2A and 2B). This suggests that amino acids missing in HNT2RS compared to HNT2RL may contribute to agonist binding and/or coupling to G proteins.

GTP sensitivity. These radioligand binding assays were performed in 96-well microtiter plates using 1×binding buffer (50 mM HEPES, pH 7.4, 10 mM MgCl$_2$, 0.4% BSA, pH 7.4) containing protease inhibitors (5 μg/ml leupeptin, 5 μg/ml aprotinin, 100 μg/ml bacitracin, and 100 μg/ml benzamidine). All components were diluted in 1×binding buffer containing protease inhibitors and added to the microtiter plate wells in the following order: binding buffer, non-radiolabeled ligand, GTPγS, [³H] neurotensin (New England Nuclear, 100 Ci/mmol, original stock is 9 μM). Wells A1–6 were repeated for each membrane preparation to be tested for GTP sensitivity. Binding reactions were initiated by adding 5–100 μg of membrane protein in a 170 μl volume. Final reaction volume was 200 μl/well.

TABLE 3

GTP Sensitivity Assay Conditions

| Well | Buffer | 100 μM Neurotensin | 1 mM GTPγS | 200 nM [³H]NT | Volume of Membrane |
|---|---|---|---|---|---|
| A1, 2 | 20 μl | 0 μl | 0 μl | 10 μl | 170 μl |
| A3, 4 | 0 μl | 20 μl | 0 μl | 10 μl | 170 μl |
| A5, 6 | 0 μl | 0 μl | 20 μl | 10 μl | 170 μl |

The microtiter plate was placed on a rotary shaker at 200 rpm and incubated at room temperature for 2 hours. Free radioligand was separated from bound ligand by rapid filtration through a glass fiber (GF/C) filter plate pretreated with 0.3% polyethyleneimine using a Packard cell harvester. The filter plates were then washed several times with cold (4° C.) binding buffer lacking BSA. After the filter plates were dried in a 37° C. incubator for 2 hours, 25 μl Microscint scintillation fluid (Packard) was added to each well and the plate was counted in a Packard Top Count scintillation counter.

TABLE 4

GTP Sensitivity of [³H]NT Binding

| Receptor | Specific [³H]NT Bound | Specific [³H]NT Bound in Presence of 100 μM GTPγS | % Decrease in [³H]NT Bound in Presence of 100 μM GTPγS |
|---|---|---|---|
| HNT2R | 575 cpm | 279 cpm | 51.5% |
| HNT2RS | 697 cpm | 451 cpm | 35.3% |

As shown in Table 4, 100 μM GTPγS decreases the specific [³H]NT binding in CHO-K1 membranes stably expressing either HNT2R or HNT2RS. Such GTP sensitivity suggests that these receptor isoforms are coupled to G proteins.

EXAMPLE 2

Calcium Mobilization Assay

Cells are harvested from a confluent 15 cm dish with 10 mls PBS/EDTA, pelleted (1500×g, 10 min) and resuspended in 10 ml DMEM media containing 250 μM sulfinpyrazone and 0.1% BSA. (Sulfinpyrazone prevents FURA-2 from entering the intracellular calcium stores, thus preventing fluorescent "hot spots".) The cells are counted and resuspended to a density of 0.5×10⁶ cells/ml in DMEM media (15 ml). The cells are then aliquoted in appropriate volumes for at least 10–15 determinations. FURA-2-A/M (Molecular Probes) is added to the cells to a final concentration of 5 μM. This is a 1:1000 dilution of the stock 5 mM FURA-2-A/M solution. The cells are incubated at 37° C. for 30 min in the dark. The cells are pelleted and resuspended first in DMEM containing 250 μM sulfinpyrazone and 0.1% BSA, then pelleted again and resuspended in HBS (Hank's Balanced Salt) containing 250 μM sulfinpyrazone. The cells are pelleted for a final time and resuspended in HBS containing 250 μM sulfinpyrazone to a density of 0.25–0.5×10⁶ cells/ml. At this point, the cells can be stored at room temperature in the dark until used for calcium measurements.

Intracellular calcium mobilizations can be measured with a Perkin-Elmer Luminescence spectrophotometer LS50B and the Fast Filter method program. Standard excitation ratio wavelengths for FURA-2 A/M are 340 and 380 nm, respectively, for the ion bound and free dye species and the emission wavelength is 510 nm. A typical experiment consists of adding 3 ml cell suspension loaded with FURA-2 A/M dye to a cuvette containing a mini stir bar. Cells are prewarmed for a few minutes in a 37° C. water bath. They are then placed in the instrument's cuvette holder, which has a stirring platform and a heat jacket preset at 37° C. Calcium chloride is added to a final concentration of 2 mM. The program is run for 2 minutes, 30 seconds to allow baseline stabilization. Agonist (30 µl of 100×stock) is added. The fluorescent ratiogram is collected for approximately 145 seconds. After this data is collected, a calibration ratiogram is obtained by adding 50 µM digitonin (30 µl of 100×stock) and then 20 seconds later, 5 mM EGTA (30 µl of 100×stock) is added. The values in the calibration are applied to the sample data to determine actual $Ca^{+2}$ ion concentrations. An antagonist experiment consists of preincubating cells with antagonist for 30 seconds prior to initiating the run described above. Data are analyzed in two ways: peak height and area under the curve (AUC) using GraphPad Prism. Ligand binding affinity ($K_i$) and agonist efficacy and potency ($EC_{50}$, mobilization of intracellular calcium) are also calculated using GraphPad Prism.

EXAMPLE 3

Cyclic AMP [$^{125}$I]Scintillation Proximity Assay

1. Harvest cells with PBS (without calcium, without magnesium)+2 mM EDTA. Pellet cells. Resuspend cell pellets in 2 ml DMEM containing 25 mM HEPES and 100 µM IBMX (isobutylmethylxanthine, a phosphodiesterase inhibitor) prewarmed to 37° C. Incubate cells at 37° C. for thirty minutes.

2. Count cells and adjust to 2×10⁶ cells/ml (100,000 cells/50 µl) with DMEM containing 25 mM HEPES and 100 µM IBMX.

3. Activate cells by adding the following reagents to a 96 well microtiter plate (in duplicate):

TABLE 5 cAMP Activation Conditions

| Well | Medium | 1 mM Forskolin | 100 µM NT or Test Compound |
|---|---|---|---|
| A1–2 (basal) | 50 µl | 0 µl | 0 µl |
| B1–2 | 40 µl | 10 µl | 0 µl |
| C1–2 | 35 µl | 10 µl | 5 µl |

Add 100,000 cells in 50 µl to each well. Incubate microtiter plate at 37° C. for 10 minutes.

4. Terminate activation by adding 100 µl 0.2 N HCl to each well. Mix by shaking on an orbital shaker at 200 rpm for 30 minutes. Neutralize reaction by adding 10 µl 2.5 N NaOH to each well. Mix by shaking on an orbital shaker at 200 rpm for two minutes. Plate can be stored at −20° C. until needed or cAMP measurements can be made directly.

5. Measure accumulated cAMP levels by using the cAMP [$^{125}$I]SPA kit (Amersham Life Science).

A. Using 12×75 mm tubes, prepare 7 standard levels of cAMP by making serial dilutions of the stock non-acetylation standard (256 pmol/ml). The 7 standard cAMP levels are 0.2 pmol, 0.4 pmol, 0.8 pmol, 1.6 pmol, 3.2 pmol, 6.4 pmol, and 12.8 pmol.

B. Pipet the following reagent volumes into wells of a 96 well Packard polystyrene optiplate.

TABLE 6 cAMP Assay Conditions

| Well | Buffer | Standards | Samples* |
|---|---|---|---|
| AB1 (NSB) | 100 µl | 0 µl | 0 µl |
| AB2 (zero standards) | 50 | 0 | 0 |
| AB3 | 0 | 50 µl (0.2 pmol) | 0 |
| AB4 | 0 | 50 µl (0.4 pmol) | 0 |
| AB5 | 0 | 50 µl (0.8 pmol) | 0 |
| AB6 | 0 | 50 µl (1.6 pmol) | 0 |
| AB7 | 0 | 50 µl (3.2 pmol) | 0 |
| AB8 | 0 | 50 µl (6.4 pmol) | 0 |
| AB9 | 0 | 50 µl (12.8 pmol) | 0 |
| AB10 | 40 | 0 | 10 µl A1 |
| AB11 | 40 | 0 | 10 µl A2 |
| AB12 | 40 | 0 | 10 µl B1 |
| CD1 | 40 | 0 | 10 µl B2 |
| CD2 | 40 | 0 | 10 µl C1 |
| CD3 | 40 | 0 | 10 µl C2 |

C. Pipette 50 µl of [$^{125}$I] cAMP into all wells.
   D. Pipette 50 µl of antiserum into all wells except the NSB wells.
   E. Place SPA anti-rabbit reagent on to a magnetic stirrer and adjust speed to ensure a homogeneous suspension. Add 50 µl SPA anti-rabbit reagent to all the wells. Each well should now contain a total volume of 200 µl.
   F. Shake on orbital shaker at 200 rpm, room temperature, overnight.
   G. Determine the amount of [$^{125}$I]cAMP bound by counting the optiPlate in a Packard Top Count scintillation counter.

EXAMPLE 4

Fluorescent Ca++ Mobilization Assay for Neurotensin Receptors

SK-N-MC cells expressing human NT2RL (long form) and NT2RS (short form) were harvested with 10 mls PBS/EDTA. The cells were centifuged (1000×g, 10 minutes) and resuspended in 10 ml DMEM containing 250 µM sulfinpyrazone and 0.1% BSA. The cells were resuspended at a density of 0.5×10⁶ cells/ml in media (15 ml), and the calcium mobilization assay was run as described in Example 2. The cells were then assayed for neurotensin-stimulated, and in the case of SK-N-MC cells expressing HNT2RS, thrombin-stimulated calcium mobilization using a Perkin-Elmer LS50B fluorometer.

Figure 3A:
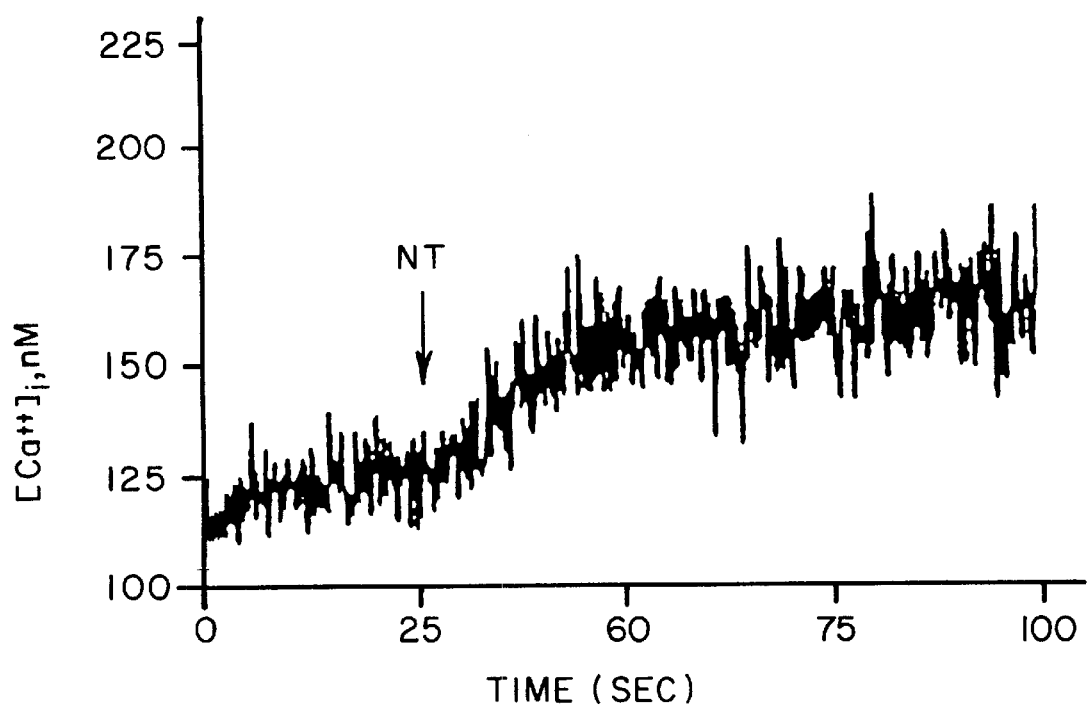
FIGS. 3A, B and C. Calcium mobilization assay of SK-N-MC (human) or non-transformed neuroblastoma cells in response to neurotensin A: Cells transformed with HNT2RL. B: Cells transformed with HNT2RS (B). C: Non-transformed (wild-type) cells.
Figure 3B:
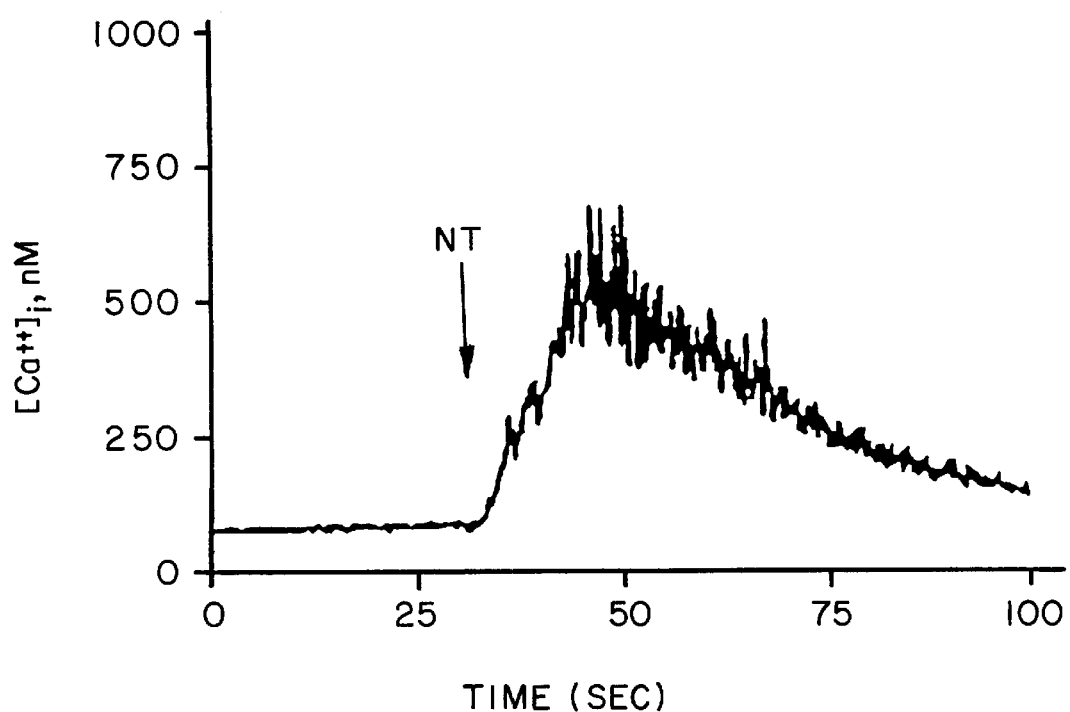
Figure 3C:
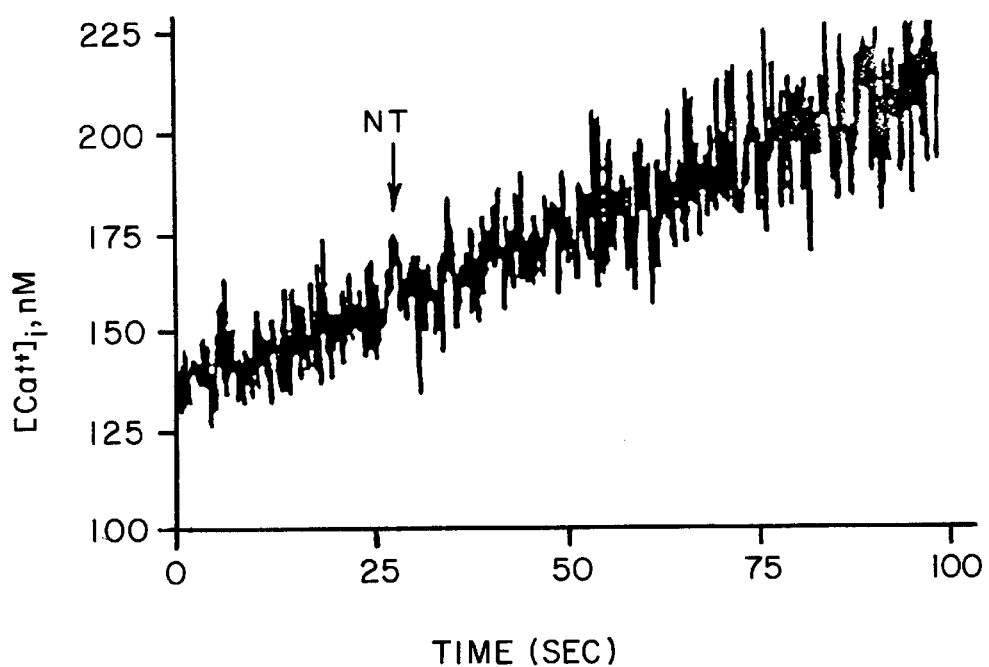

The results of this assay are shown in FIG. 3. Cells expressing HNT2RL and HNT2RS were clearly responsive to neurotensin (FIGS. 3A and 3B, respectively). Cells expressing HNT2RS were responsive to neurotensin to the same degree as thrombin (data not shown). SK-N-MC cells express a thrombin receptor endogenously, so thrombin serves as an internal control for calcium mobilization.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Patents, patent applications, and publications are cited throughout this application, the disclosures of which are incorporated herein by reference in their entireties.

What is claimed is:

1. An isolated nucleic acid molecule comprising a sequence that encodes a functional human neurotensin subtype 2 receptor (HNT2R), wherein said HNT2R binds neurotensin or a neurotensin agonist and has a feature selected from the group consisting of:

(a) an amino acid sequence of SEQ ID NO:2 lacking residues 281 to 300; and (b) an amino acid sequence comprising SEQ ID NO:6.

2. An isolated nucleic acid according to claim 1, wherein said HNT2R has 391 amino acids.

3. An isolated nucleic acid according to claim 1, wherein said HNT2R comprises an amino acid sequence of SEQ ID NO:6.

4. An isolated nucleic acid according to claim 1, wherein said HNT2R comprises an amino acid sequence corresponding to an amino acid sequence from residue 209 to residue 281 of SEQ ID NO:4.

5. An isolated nucleic acid according to claim 4, wherein said HNT2R has an amino acid sequence as depicted in SEQ ID NO:4.

6. An isolated nucleic acid according to claim 5, which has a nucleotide sequence as depicted in SEQ ID NO:3.

7. An isolated nucleic acid comprising a sequence that encodes a deletion variant of HNT2R which is functional, wherein said HNT2R deletion variant binds neurotensin or a neurotensin agonist and has an amino acid sequence of SEQ ID NO:2 lacking part of an intracellular domain 3 (IC3).

8. An isolated nucleic acid according to claim 1, wherein said sequence that encodes HNT2R is operatively associated with an expression control sequence.

9. An isolated nucleic acid according to claim 8 which is a plasmid.

10. A plasmid according to claim 9 which is pJSHNT2RS.

11. An isolated host cell transfected with said nucleic acid according to claim 8.

12. A host according to claim 11 which is eukaryotic cell.

13. A host cell according to claim 12 which is selected from the group consisting of a rat pituitary somotomammotrophic cell, a human neuroblastoma cell, and a Chinese hamster ovary cell.

14. A method for producing HNT2R comprising culturing said cell according to claim 11 under conditions that permit expression of HNT2R.

15. A method for identifying a compound that binds to HNT2R comprising detecting binding of a test compound to said HNT2R expressed by said cell according to claim 11.

16. A method according to claim 15, wherein detecting binding comprises detecting competition of binding of a labeled neurotensin receptor binding partner by said compound.

17. A method according to claim 15, wherein said neurotensin receptor binding partner is selected from the group consisting of neurotensin, N-terminal acetylated neurotensin (8–13), neurotensin(9–13), SR48692, and levocabastine.

18. A method according to claim 15, wherein said HNT2R is present in a cell membrane preparation.

19. A method according to claim 15, wherein detecting binding of said test compound to HNT2R comprises detecting changes in intracellular calcium concentration in said cell.

20. A method according to claim 15, wherein detecting binding of said test compound to HNT2R comprises detecting changes in cAMP accumulation in said cell.

21. A method for making a cell responsive to neurotensin comprising transforming said cell with the nucleic acid molecule according to claim 8.

22. A method according to claim 21, wherein said cell is a eukaryotic cell.

23. A method according to claim 21, wherein said sequence that encodes HNT2R encodes an HNT2R of 391 amino acids.

24. The isolated nucleic acid according to claim 7, wherein said HNT2R further lacks part of tansmembrane domains 6 (TM6).

25. An isolated nucleic acid wherein at least 95% of the nucleotides are identical to SEQ ID NO:3, which isolated nucleic acid encodes an human neurotensin type 2 receptor that binds neurotensin or a neurotensin agonist.

* * * * *